(12) United States Patent
Rao et al.

(10) Patent No.: US 6,787,353 B1
(45) Date of Patent: *Sep. 7, 2004

(54) LINEAGE-RESTRICTED NEURONAL PRECURSORS AND METHODS OF ISOLATION

(75) Inventors: Mahendra S. Rao, Salt Lake City, UT (US); Margot Mayer-Proschel, Sandy, UT (US); Anjali J. Kalyani, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/109,858

(22) Filed: Jul. 2, 1998

Related U.S. Application Data

(63) Continuation-in-part of application No. 08/909,435, filed on Jul. 4, 1997.

(51) Int. Cl.$^7$ .................................................. C12N 5/08

(52) U.S. Cl. ...................................... 435/368; 435/377

(58) Field of Search ................................ 435/352, 366, 435/368, 377, 345, 350, 351, 455; 424/932

(56) References Cited

U.S. PATENT DOCUMENTS

| | | | |
|---|---|---|---|
| 5,087,570 A | | 2/1992 | Weissman et al. |
| 5,175,103 A | * | 12/1992 | Lee et al. ................. 435/172.3 |
| 5,411,883 A | * | 5/1995 | Boss et al. ............... 435/240.2 |
| 5,589,376 A | | 12/1996 | Anderson et al. |
| 5,753,506 A | * | 5/1998 | Johe ........................... 435/377 |

FOREIGN PATENT DOCUMENTS

| | | | |
|---|---|---|---|
| WO | 93/01275 | * | 1/1993 |

OTHER PUBLICATIONS

Geysen et al. J. Molecular Recognition 1:32–41, 1988.*
Rao et al., Society For Neuroscience, 26th Annual Meeting, 22:527, Abstract #215.12, 1996.*
Svendsen et al., TINS, 22:357–364., 1999.*
Seamark, Reprod. Fertil. Dev., 6:653–657, 1994.*
Mullins et al., J. Clin. Invest., 98:S37–S40, 1996.*
Bradley et al., Bio/Technology, 10:534–539, 1992.*
Sanberg et al., In Advances in Gene Technology: Molecular Biology In The Conquest Of Disease, Nucleic Acids Symposium Series, #38, pp. 139–142, Oxford Press, 1998.*
Sabate et al., Clinical Neuroscience, 3:317–321, 1996.*
Scheffler et al., TINS, 22:348–357, 1999.*
Blass–Kampmann et al., J. Neuroscience Research, 37:359–373, 1994.*
Gage, F.H. et al., *Isolation, Characterization and Use of Stem Cells from the CNS*, 18 Ann. Rev. Neurosci. 159–92 (1995).

Marvin, M. et al., *Multipotential Stem Cells in the Vertebrate CNS*, 3 Semin. Cell. Biol. 401–11 (1992).
Davis, A.A. et al., *A Self–Renewing Multipotential Stem Cell in Embryonic Rat Cerebral Cortex*, 362 Nature 363–72 (1994).
Gritti, A.G. et al., *Multipotential Stem Cells from the Adult Mouse Brain Proliferate and Self–Renew in Response to Basic Fibroblast Growth Factor*, 16 J. Neurosci. 1091–1100 (1996).
Reynolds, B.A. et al., *A Multipotent EGF–Responsive Stiatal Embryonic Progenitor Cell Produces Neurons and Astrocytes*, 12 J. Neurosci. 4565–74 (1992).
Reynolds, B.A. et al., *Clonal and Population Analyses Demonstrate that an EGF–Responsive Mammalian Embryonic CNS Precursor is a Stem Cell*, 175 Developmental Biol. 1–13 (1996).
Williams, B.P. et al., *The Generation of Neurons and Oligodendrocytes from a Common Precursor Cell*, 7 Neuron 685–93 (1991).
Kilpatrick, T.J. et al., *Cloned Multipotential Precursors from the Mouse Cerebrum Require FGF–2, Whereas Glial Restricted Precursors are Stimulated with Either FGF–2 or EGF*, 15 J. Neurosci. 3653–61 (1995).
Price, J. et al., *Lineage Analysis in the Vertebrate Nervous System by Retrovirus–Mediated Gene Transfer*, 84 Developmental Biol. 156–60 (1987).
Williams, B., *Precursor Cell Types in the Germinal Zone of the Cerebral Cortex*, 17 BioEssays 391–93 (1995).

(List continued on next page.)

*Primary Examiner*—Gary Kunz
*Assistant Examiner*—Robert C. Hayes
(74) *Attorney, Agent, or Firm*—Licata & Tyrrell P.C.

(57) ABSTRACT

A self-renewing restricted stem cell population has been identified in developing (embryonic day 13.5) spinal cords that can differentiate into multiple neuronal phenotypes, but cannot differentiate into glial phenotypes. This neuronal-restricted precursor (NRP) expresses highly polysialated or embryonic neural cell adhesion molecule (E-NCAM) and is morphologically distinct from neuroepithelial stem cells (NEP cells) and spinal glial progenitors derived from embryonic day 10.5 spinal cord. NRP cells self renew over multiple passages in the presence of fibroblast growth factor (FGF) and neurotrophin 3 (NT-3) and express a characteristic subset of neuronal epitopes. When cultured in the presence of RA and the absence of FGF, NRP cells differentiate into GABAergic, glutaminergic, and cholinergic immunoreactive neurons. NRP cells can also be generated from multipotent NEP cells cultured from embryonic day 10.5 neural tubes. Clonal analysis shows that E-NCAM immunoreactive NRP cells arise from an NEP progenitor cell that generates other restricted CNS precursors. The NEP-derived E-NCAM immunoreactive cells undergo self renewal in defined medium and differentiate into multiple neuronal phenotypes in mass and clonal culture. Thus, a direct lineal relationship exists between multipotential NEP cells and more restricted neuronal precursor cells present in vivo at embryonic day 13.5 in the spinal cord. Methods for treating neurological diseases are also disclosed.

7 Claims, 10 Drawing Sheets

OTHER PUBLICATIONS

Anderson, D.J., *The Neural Crest Lineage Problem: Neuropoiesis?*, 3 Neuron 1–12 (1989).

Ray, J. et al., *Spinal Cord Neuroblasts Proliferate in Response to Basic Fibroblast Growth Factor*, 14 J. Neurosci. 3548–64 (1994).

Sommer, L. et al., *The Cellular Function of MASH1in Autonomic Neurogenesis*, 15 Neuron 1245–58 (1995).

Bignami, A. et al., *Localization of the Glial Fibrillary Acidic Protein in Astrocytes by Immunofluorescence*, 43 Brain Res. 429–35 (1972).

Geisert, E. et al., *The Neoronal Response to Injury as Visualized by Immunostaining of Class β–tubulin in the Rat*, 102 Neurosci. Lett. 137–41 (1989).

Lendahl, U. et al., *CNS Stem Cells Express a New Class of Intermediate Filament Protein*, 60 Cell 585–95 (1990).

Mayer, M. et al. *Ciliary Neurotrophic Factor and Leukemia Inhibitory Factor Promote the Generation, Maturation, and Survival of Oligodendrocytes*, 120 Development 142–53 (1994).

Wysocki, L. et al., *"Panning" for Lymphocytes: A Method for Cell Selection*, 75 Proc. Nat'l Acad. Sci. USA 2844–48 (1978).

Bottenstein, J. et al., *Growth of a Rat Neuroblastoma Cell Line in serum–free Supplemented Medium*, 76 Proc. Natl Acad. Sci. USA 514–17 (1979).

Mayer Proschel et al., "Human neural precursor cells—an in vitro characterization" Clinical Neuroscience Res. 2002 2:58–69.

Carpenter et al. "Enrichment of Neurons and Neural Precursors from Human Embryonic Stem Cells" Exp. Neurol. 2001 172:383–397.

Dodd et al. *Neuron* (1988) 1 (2) :105–16.

Finne et al. *Biochem. Biophys. Res. Commun.* (1983) 122:482–487.

Sadoul et al. *Nature* (London) (1983) 304:347–349.

\* cited by examiner

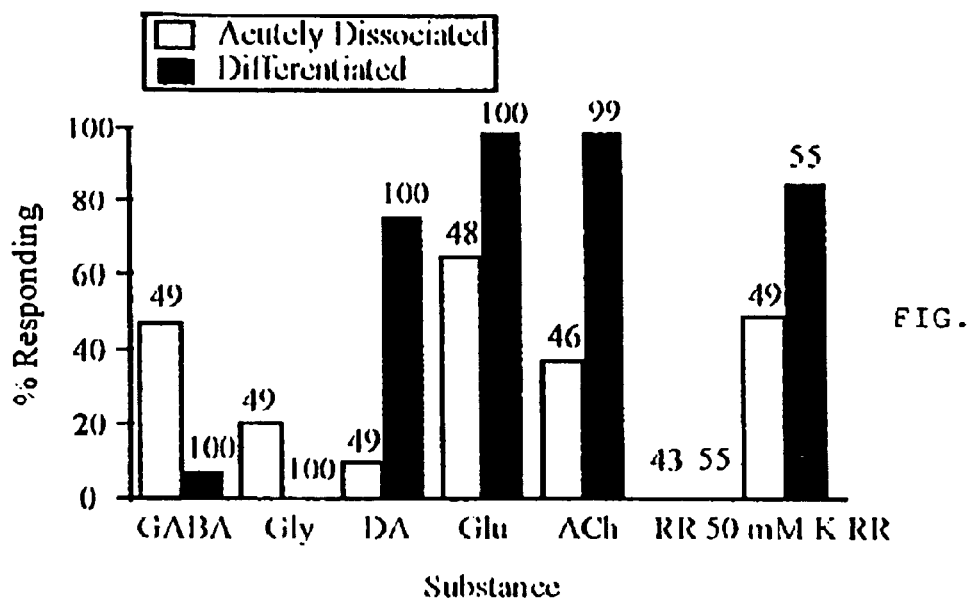
FIG. 3
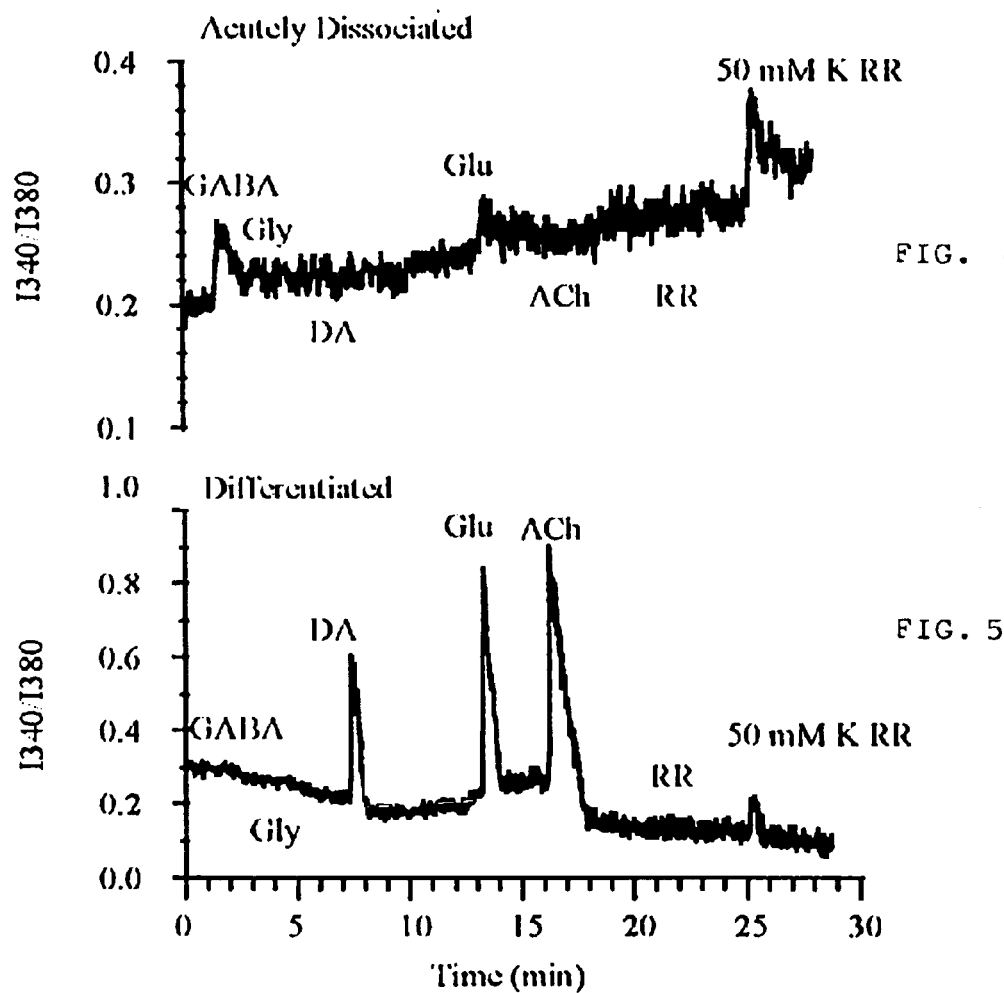
FIG. 4
FIG. 5

LINEAGE-RESTRICTED NEURONAL PRECURSORS AND METHODS OF ISOLATION

CROSS-REFERENCE TO RELATED APPLICATIONS

This application is a continuation-in-part of application Ser. No. 08/909,435, filed Jul. 4, 1997.

STATEMENT REGARDING FEDERALLY SPONSORED RESEARCH OR DEVELOPMENT

This invention was made with government support under a FIRST award and a Multidisciplinary Basic Cancer Research Training Grant Graduate Fellowship from the National Institutes of Health. The government has certain rights in the invention.

BACKGROUND OF THE INVENTION

This invention relates to lineage-restricted intermediate precursor cells and methods of making and using thereof. More particularly, the invention relates to neuronal-restricted precursors (NRP's) isolated from mammalian embryos, neuroepithelial stem (NEP) cells, or embryonic stem (ES) cells. These neuronal-restricted precursors are capable of self-renewal and differentiation into neurons, but not into glia, i.e. astrocytes and oligodendrocytes. Methods of generating, isolating, culturing, transfecting, and transplanting such neuronal-restricted precursor cells are also described.

Multipotent cells with the characteristics of stem cells have been identified in several regions of the central nervous system and at several developmental stages. F. H. Gage et al., Isolation, Characterization and Use of Stem Cells from the CNS, 18 Ann. Rev. Neurosci. 159–92 (1995); M. Marvin & R. McKay, Multipotential Stem Cells in the Vertebrate CNS, 3 Semin. Cell. Biol. 401–11 (1992); R. P. Skoff, The Lineages of Neuroglial Cells, 2 The Neuroscientist 335–44 (1996). These cells, often referred to as neuroepithelial stem cells (NEP cells), have the capacity to undergo self renewal and to differentiate into neurons, oligodendrocytes, and astrocytes, thus representing multipotent stem cells. A. A. Davis & S. Temple, A Self-Renewing Multipotential Stem Cell in Embryonic Rat Cerebral Cortex, 362 Nature 363–72 (1994); A. G. Gritti et al., Multipotential Stem Cells from the Adult Mouse Brain Proliferate and Self-Renew in Response to Basic Fibroblast Growth Factor, 16 J. Neurosci. 1091–1100 (1996); B. A. Reynolds et al., A Multipotent EGF-Responsive Striatal Embryonic Progenitor Cell Produces Neurons and Astrocytes, 12 J. Neurosci. 4565–74 (1992); B. A. Reynolds & S. Weiss, Clonal and Population Analyses Demonstrate that an EGF-Responsive Mammalian Embryonic CNS Precursor is a Stem Cell, 175 Developmental Biol. 1–13 (1996); B. P. Williams et al., The Generation of Neurons and Oligodendrocytes from a Common Precursor Cell, 7 Neuron 685–93 (1991).

The nervous system also contains precursor cells with restricted differentiation potentials. T. J. Kilpatrick & P. F. Bartlett, Cloned Multipotential Precursors from the Mouse Cerebrum Require FGF-2, Whereas Glial Restricted Precursors are Stimulated with Either FGF-2 or EGF, 15 J. Neurosci. 3653–61 (1995); J. Price et al., Lineage Analysis in the Vertebrate Nervous System by Retrovirus-Mediated Gene Transfer, 84 Developmental Biol. 156–60 (1987); B. A. Reynolds et al., supra; B. A. Reynolds & S. Weiss, supra; B. Williams, Precursor Cell Types in the Germinal Zone of the Cerebral Cortex, 17 BioEssays 391–93 (1995); B. P. Williams et al., supra. The relationship between multipotent stem cells and lineage restricted precursor cells is still unclear. In principal, lineage restricted cells could be derived from multipotent cells, but this is still a hypothetical possibility in the nervous system with no direct experimental evidence. Further, no method of purifying such precursors from multipotent cells has been described.

As has been shown in copending U.S. patent application Ser. No. 08/852,744, entitled "Generation, Characterization, and Isolation of Neuroepithelial Stem Cells and Lineage Restricted Intermediate Precursor," filed May 7, 1997, hereby incorporated by reference in its entirety, NEP cells grow on fibronectin and require fibroblast growth factor (FGF) and an as yet uncharacterized component present in chick embryo extract (CEE) to proliferate and maintain an undifferentiated phenotype in culture. The growth requirements of NEP cells are different from neurospheres isolated from E14.5 cortical ventricular zone cells. B. A. Reynolds et al., supra; B. A. Reynolds & S. Weiss, supra; WO 9615226; WO 9615224; WO 9609543; WO 9513364; WO 9416718; WO 9410292; WO 9409119. Neurospheres grow in suspension culture and do not require CEE or FGF, but are dependent on epidermal growth factor (EGF) for survival. FGF itself is not sufficient for long term growth of neurospheres, though FGF may support their growth transiently. NEP cells, however, grow in adherent culture, are FGF dependent, do not express detectable levels of EGF receptors, and are isolated at a stage of embryonic development prior to which it has been possible to isolate neurospheres. Thus, NEP cells may represent a multipotent precursor characteristic of the brain stem and spinal cord, while neurospheres may represent a stem cell more characteristic of the cortex. Nonetheless, NEP cells provide a model system for studying the principles of lineage restriction from multipotent stem cells or precursor cells of the central nervous system. The principles elucidated from the study of NEP cells are expected to be broadly applicable to all CNS precursor cells sufficiently multipotent to generate both neurons and glia. Thus, the present application is intended to be applicable to any CNS precursor cells regardless of their site of derivation as long as they are able to differentiate to both neurons and glial cells.

U.S. Pat. No. 5,589,376, to D. J. Anderson and D. L. Stemple, discloses mammalian neural crest stem cells and methods of isolation and clonal propagation thereof, but fails to disclose cultured NEP cells, cultured lineage restricted precursor cells, and methods of generating, isolating, and culturing thereof. Neural crest cells differentiate into neurons and glia of the peripheral nervous system (PNS), whereas the neuroepithelial stem cells differentiate into neurons and glia of the central nervous system (CNS).

U.S. Ser. No. 08/909,435, filed Jul. 4, 1997, for "Isolation of Lineage Restricted Neuronal Precursors," hereby incorporated by reference in its entirety, describes neuronal restricted precursor (NRP) cells that are capable of differentiating into neurons, but not into glial cells. It was shown that NRP cells can be isolated from NEP cells, as well as directly from embryonic spinal cords.

U.S. Ser. No. 08/980,850, filed Nov. 29, 1997, for "Lineage Restricted Glial Precursors from the Central Nervous System," hereby incorporated by reference in its entirety, describes glial restricted precursor (GRP) cells that are capable of differentiating into oligodendrocytes, A2B5$^+$ process-bearing astrocytes, and A2B5$^-$ fibroblast-like astrocytes, but not into neurons. GRP cells can be isolated from differentiating NEP cells, as well as CNS tissue, and differ from oligodendrocyte-type-2 astrocyte (O-2A) progenitor cells in growth factor requirements, morphology, and progeny.

In U.S. patent application Ser. No. 09/073,881, filed May 6, 1998, for "Common Neural Progenitor for CNS and PNS," hereby incorporated by reference in its entirety, it was shown that NEP cells can be induced to differentiate into neural crest cells as well as other cells of the CNS and PNS.

The neuron-restricted precursor cells described herein are distinct from the NEP cells, GRP cells, neurospheres, and neural crest stem cells that have been described elsewhere. NEP cells are capable of differentiating into neurons or glia whereas NRPs can differentiate into neurons, but not glia, and NEP cells and NRPs display distinct cell markers. GRP cells can differentiate into glia, but not neurons. As mentioned above, neurospheres grow in suspension culture and do not require CEE or FGF, but are dependent on EGF for survival, whereas NRP cells grow in adherent culture and do not express detectable levels of EGF receptors. Further, neural crest cells differentiate into neurons and glia of the peripheral nervous system (PNS), whereas NRP cells differentiate into neurons of the central nervous system (CNS). NRP cells express polysialated or embryonic neural cell adhesion molecule (E-NCAM), but NEP cells, neurospheres, GRP cells, and neural crest cells do not. Therefore, NRP cells are different in their proliferative potential, expression of cell markers, and nutritional requirements from these other cell types.

The ability to isolate and grow mammalian neuronal-restricted precursor cells in vitro allows for of using pure populations of neurons for transplantation, discovery of genes specific to selected stages of development, generation of cell-specific antibodies for therapeutic and diagnostic uses such as for targeted gene therapy, and the like. Further, NRP cells can be used to generate subpopulations of neurons with specific properties, i.e. motoneurons and other neuronal cells for analyzing neurotransmitter functions and small molecules in high throughput assays.

Moreover, the methods of obtaining NRP cells from NEP cells or embryonic stem (ES) cells provides for a ready source of a large number of post-mitotic neurons. Post-mitotic cells obtained from a tumor cell line are already being commercially marketed (e.g., Clontech, Palo Alto, Calif.). The present invention is also necessary to understand how multipotent neuroepithelial stem cells become restricted to the various neuroepithelial derivatives. In particular, culture conditions that allow the growth and self-renewal of mammalian neuronal-restricted precursor cells are desirable so that the particulars of the development of these mammalian stem cells can be ascertained. This is desirable because a number of tumors of neuroepithelial derivatives exist in mammals, particularly humans. Knowledge of mammalian neuroepithelial stem cell development is therefore needed to understand these disorders in humans.

In view of the foregoing, it will be appreciated that isolated populations of mammalian lineage restricted neuronal precursor cells and methods of generating, isolating, culturing, transfecting, and transplanting such cells would be significant advancements in the art.

BRIEF SUMMARY OF THE INVENTION

It is an object of the present invention to provide isolated (pure) populations of mammalian neuronal-restricted precursor cells and their progeny.

It is another object of the invention to provide methods of generating, isolating, culturing, and regenerating of mammalian lineage-restricted neuronal precursor cells and their progeny.

It is yet another object of the invention to provide a method for the generation of lineage-restricted neuronal precursor cells from a CNS multipotent precursor cell able to generate both neurons and glia.

It is a still further object of the invention to provide pure differentiated populations of neuronal cells derived from lineage-restricted neuronal precursor cells.

It is still another object of the invention to provide methods of transfecting and transplanting such neuronal restricted precursor cells.

These and other objects can be achieved by providing an isolated, pure population of mammalian CNS neuron-restricted precursor cells. Preferably, such neuron-restricted precursor cells are capable of self-renewal, differentiation to CNS neuronal cells but not to CNS glial cells, and expressing embryonic neural cell adhesion molecule (E-NCAM), but not expressing a ganglioside recognized by A2B5 antibody. These neuron-restricted precursor cells may or may not express nestin or β-III tubulin. Thus, embryonic neural cell adhesion molecule (E-NCAM) is a defining antigen for these cells. The NRP cells are able to differentiate into neurons that are capable of releasing and responding to neurotransmitters. These neurons can demonstrate receptors for these neurotransmitters, and such cells are capable of expressing neurotransmitter-synthesizing enzymes. The NRP cells are also capable of differentiating into neurons that can form functional synapses and/or develop electrical activity. The NRP cells are also capable of stably expressing at least one material selected from the group consisting of growth factors for such cells, differentiation factors for such cells, maturation factors for such cells, and combinations of any of these. Further, the present neuron-restricted precursor cells may be selected, chosen, and isolated from human primates, non-human primates, equines, canines, felines, bovines, porcines, ovines, lagomorphs, and rodents.

A method of isolating a pure population of mammalian CNS neuron-restricted precursor cells comprises the steps of:

(a) isolating a population of mammalian multipotent CNS stem cells capable of generating both neurons and glia;

(b) incubating the multipotent CNS stem cells in a medium configured for inducing such cells to begin differentiating;

(c) purifying from the differentiating cells a subpopulation of cells expressing a selected antigen defining neuron-restricted precursor cells; and (d) incubating the purified subpopulation of cells in a medium configured for supporting adherent growth thereof.

A preferred selected antigen defining neuron-restricted precursor cells is embryonic neural cell adhesion molecule. Preferably, the step of purifying the NRP cells comprises a procedure selected from the group consisting of specific antibody capture, fluorescence activated cell sorting, and magnetic bead capture. Specific antibody capture is especially preferred. In a preferred embodiment, the mammalian multipotent CNS stem cells are neuroepithelial stem cells. A preferred procedure for isolating a population of CNS neuroepithelial stem cells comprises:

(a) removing a CNS tissue from a mammalian embryo at a stage of embryonic development after closure of the neural tube but prior to differentiation of cells in the neural tube;

(b) dissociating cells comprising the neural tube removed from the mammalian embryo;

(c) plating the dissociated cells in feeder-cell-independent culture on a substratum and in a medium configured for supporting adherent growth of the neuroepithelial stem cells comprising effective amounts of fibroblast growth factor and chick embryo extract; and (d) incubating the plated cells at a temperature and in an atmosphere conducive to growth of the neuroepithelial stem cells.

Preferably, the mammalian embryo is selected from the group consisting of human and non-human primates, equines, canines, felines, bovines, porcines, ovines, lagomorphs, and rodents. It is also preferred that the substratum is selected from the group consisting of fibronectin, vitronectin, laminin, and RGD peptides. In a preferred embodiment, the medium comprises effective amounts of fibroblast growth factor and neurotrophin 3 (NT-3).

A method of isolating a pure population of mammalian CNS neuron-restricted precursor cells comprises the steps of:

(a) removing a sample of CNS tissue from a mammalian embryo at a stage of embryonic development after closure of the neural tube but prior to differentiation of glial and neuronal cells in the neural tube;

(b) dissociating cells comprising the sample of CNS tissue removed from the mammalian embryo;

(c) purifying from the dissociated cells a subpopulation expressing a selected antigen defining neuron-restricted precursor cells;

(d) plating the purified subpopulation of cells in feeder-cell-independent culture on a substratum and in a medium configured for supporting adherent growth of the neuron-restricted precursor cells; and (e) incubating the plated cells at a temperature and in an atmosphere conducive to growth of the neuron-restricted precursor cells.

Preferably, the selected antigen defining neuron-restricted precursor cells is embryonic neural cell adhesion molecule. It is also preferred that the step of purifying comprises a procedure selected from the group consisting of specific antibody capture, fluorescence activated cells sorting, and magnetic bead capture. Specific antibody capture is especially preferred. It is further preferred that the mammalian embryo is selected from the group consisting of human and non-human primates, equines, canines, felines, bovines, porcines, ovines, lagomorphs, and rodents.

A method of obtaining postmitotic neurons comprises:

(a) providing neuron-restricted precursor cells and culturing the neuron-restricted precursor cells in proliferating conditions; and (b) changing the culture conditions of the neuron-restricted precursor cells from proliferating conditions to differentiating condition, thereby causing the neuron-restricted precursor cells to differentiate into postmitotic neurons.

The changing of the culture conditions preferably comprises adding retinoic acid to basal medium or withdrawing a mitotic factor from basal medium. Such a mitotic factor is fibroblast growth factor. Changing the culture conditions can also comprise adding a neuronal maturation factor to basal medium. Preferred neuronal maturation factors are selected from the group consisting of sonic hedgehog, BMP-2, BMP-4, NT-3, NT-4, CNTF, LIF, retinoic acid, brain-derived neurotrophic factor (BDNF), and combinations of any of the above.

Another preferred embodiment of the invention comprises an isolated cellular composition comprising the mammalian CNS neuron-restricted cells described herein. Another preferred embodiment of the invention comprises a pharmaceutical composition comprising a therapeutically effective amount of such composition and a pharmaceutically acceptable carrier.

A method for treating a neuronal disorder in a mammal comprises administering to such mammal a therapeutically effective amount of the isolated cellular composition comprising the mammalian CNS neuron-restricted cells described herein. Another method for treating a neuronal disorder in a mammal comprising administering to said mammal a therapeutically effective amount of such pharmaceutical composition and a pharmaceutically acceptable carrier. Such composition can be administered by a route selected from the group consisting of intramuscular administration, intrathecal administration, intraperitoneal administration, intravenous administration, and combinations of any of the above. This method can also include the administration of a member selected from the group consisting of differentiation factors, growth factors, cell maturation factors and combinations of any of the above. Such differentiation factors are preferably selected from the group consisting of retinoic acid, BMP-2, BMP-4, and combinations of any of the above.

A method for treating neurodegenerative symptoms in a mammal comprises the steps of:

(a) providing a pure population of neuronal restricted precursor cells;

(b) genetically transforming such neuronal restricted precursor cells with a gene encoding a growth factor, neurotransmitter, neurotransmitter synthesizing enzyme, neuropeptide, neuropeptide synthesizing enzyme, or substance that provides protection against free-radical mediated damage thereby resulting in a transformed population of neuronal restricted precursor cells that express such growth factor, neurotransmitter, neurotransmitter synthesizing enzyme, neuropeptide, neuropeptide synthesizing enzyme, or substance that provides protection against free-radical mediated damage; and (c) administering an effective amount of said transformed population of neuronal restricted precursor cells to such mammal.

A method or screening compounds for neurological activity comprising the steps of:

(a) providing a pure population of neuronal restricted precursor cells or derivatives thereof or mixtures thereof cultured in vitro;

(b) exposing such cells or derivatives thereof or mixtures thereof to a selected compound at varying dosages; and (c) monitoring the reaction of such cells or derivatives thereof or mixtures thereof to said selected compound for selected time periods.

A method for treating a neurological or neurodegenerative disease comprises administering to a mammal in need of such treatment an effective amount of neuronal restricted precursor cells or derivatives thereof or mixtures thereof. Such neuronal restricted precursor cells or derivatives thereof or mixtures thereof can be from either a heterologous donor or an autologous donor. The donor can be a fetus, juvenile, or adult.

A method of isolating a pure population of mammalian CNS neuron-restricted precursor cells comprises the steps of:

(a) providing a sample of mammalian embryonic stem cells;

(b) purifying from the mammalian embryonic stem cells a subpopulation expressing a selected antigen defining neuron-restricted precursor cells;

(c) plating the purified subpopulation of cells in feeder-cell-independent culture on a substratum and in a medium configured for supporting adherent growth of the neuron-restricted precursor cells; and (d) incubating the plated cells at a temperature and in an atmosphere conducive to growth of the neuron-restricted precursor cells.

BRIEF DESCRIPTION OF THE SEVERAL VIEWS OF THE DRAWINGS

FIG. 3 shows a bar graph of the number of cells responding to neurotransmitters on acutely dissociated (unshaded) and differentiated (shaded) E-NCAM$^+$ cells as measured by fura-2 calcium ion imaging: GABA ($\gamma$-amino butyric acid), Gly (glycine), DA (dopamine), Glu (glutamate), Ach (acetyl choline), RR (rat ringers solution), 50 mM K RR (rat ringers solution modified by replacing Na$^+$ with K$^+$).

FIG. 4 shows an illustrative plot of the ratio ($I_{340}/I_{380}$) of Ca$^{2+}$ responses over time from an acutely dissociated E-NCAM$^+$ cell.

FIG. 5 shows an illustrative plot of the ratio ($I_{340}/I_{380}$) of Ca$^{2+}$ responses over time from a differentiated E-NCAM$^+$ cell.

DETAILED DESCRIPTION

Figure 1:
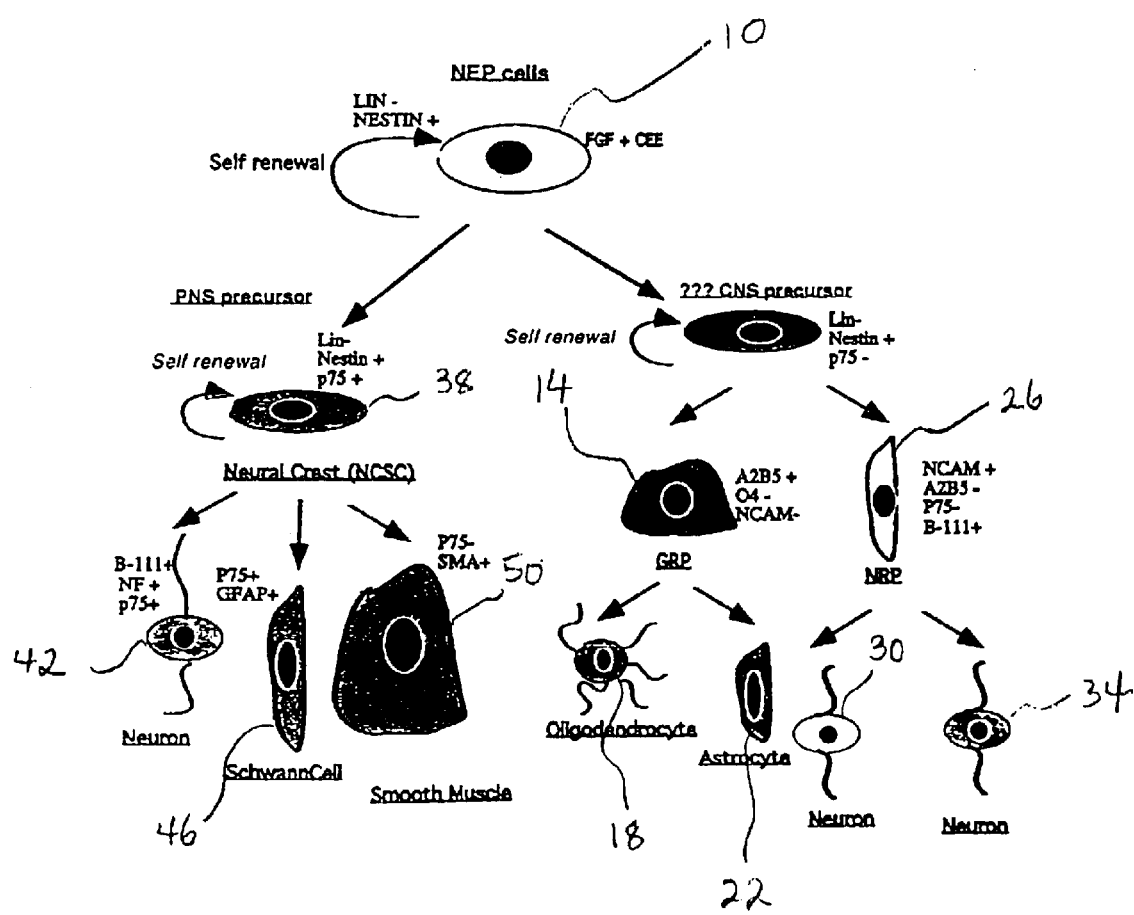
FIG. 1 shows a summary of the immunoreactivities of NEP cells and their progeny, including NRP cells.

Before the present neuronal-restricted precursor cells and methods of making and methods of use thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to "an embryo" includes reference to two or more embryos, reference to "a mitogen" includes reference to a mixture of two or more mitogens, and reference to "a factor" includes reference to a mixture of two or more factors.

In describing and claiming the present invention, the following terminology will be used in accordance with the definitions set out below.

As used herein, "self renewal" refers, for example, to the capability of a neuroepithelial stem cell to divide to produce two daughter cells, at least one of which is a multipotent neuroepithelial stem cell, or to the capability of a neuronal-restricted precursor cell to divide to produce two daughter cells, at least one of which is a neuronal-restricted precursor cell.

As used herein, "clonal density" and similar terms mean a density sufficiently low enough to result in the isolation of single, non-impinging cells when plated in a selected culture dish. An illustrative example of such a clonal density is about 225 cells/100 mm culture dish.

As used herein, "feeder-cell-independent adherent culture" and similar terms mean the growth of cells in vitro in the absence of a layer of different cells that generally are first plated on a culture dish to which the cells from the tissue of interest are then added. In feeder cell cultures, the feeder cells provide a substratum for the attachment of cells from the tissue of interest and additionally serve as a source of mitogens and survival factors. The feeder-cell-independent adherent cultures herein use a chemically defined substratum, for example fibronectin, and mitogens or survival factors are provided by supplementation of the liquid culture medium with either purified factors or crude extracts from other cells or tissues. Therefore, in feeder-cell-independent cultures, the cells in the culture dish are primarily cells derived from the tissue of interest and do not contain other cell types required to support the growth of cells derived from the tissue of interest.

As used herein, "effective amount" means an amount of a growth factor or survival factor or other factor that is nontoxic but sufficient to provide the desired effect and performance. For example, an effective amount of FGF as used herein means an amount selected so as to support self renewal and proliferation of NEP cells when used in combination with other essential nutrients, factors, and the like. An effective amount of NRP cells or derivatives thereof or mixtures thereof for transplantation refers to an amount or number of cells sufficient to obtain the selected effect. NRP cells will generally be administered at concentrations of about 5–50,000 cells/microliter. Transplantation will generally occur in volumes up to about 15 microliters per injection site. However, transplantation subsequent to surgery on the central nervous system can involve volumes many times this size. Thus, the number of cells used for transplantation is limited only by utility, and such numbers can be determined by a person skilled in the art without undue experimentation.

As used herein, "derivative" of an NRP cell means a cell derived from an NRP cell in vitro by genetic transduction, differentiation, or similar processes.

As used herein, "administering an NRP cell to a mammal means transplanting or implanting such NRP cell into CNS tissue or adjacent to such CNS tissue of a recipient. Such administration can be carried out by any method known in the art, such as surgery, with an infusion cannula, needle, and the like.

As used herein, "heterologous" refers to individuals, tissues, or cells different from a transplant recipient. The transplant donor could be from the same species or a different species as the transplant recipient. For example, a heterologous donor of NRP cells for transplantation an could be from a different species as the transplant recipient.

As used herein, "autologous" refers to self-generated or originating within the body. Thus, for example, an autologous donor of tissue or cells for transplantation is the same individual that receives the transplant. By way of further example, autologous cells are cells arising, transferred, or transplanted within an individual. In vitro manipulation may take place between harvesting of the cells and transplanting such cells or derivatives thereof, but is not required prior to transplantation.

As used herein, "transforming," "transducing," "transfection," and similar terms mean insertion or transfer of a gene or genes into NRP cells regardless of the method of insertion r transfer. Thus, transformation can be accomplished by calcium phosphate transfection, DEAE-dextran transfection, polybrene transfection, electroporation, lipofection, infection of viruses, and the like and any other methods known in the art.

The present invention is illustrated using neuron-restricted precursor cells isolated from rats, mice, and humans. The invention, however, encompasses all mammalian neuronal-restricted precursor cells and is not limited to neuronal-restricted precursor cells from rats, mice, and humans. Mammalian neuron-restricted precursor cells can be isolated from human and non-human primates, equines, canines, felines, bovines, porcines, ovines, lagomorphs, and the like.

Pluripotent stem cells in the central nervous system may generate differentiated neurons and glia either directly or through the generation of lineage-restricted intermediate precursors. In the developing retina, it appears that multipotent retinal precursors can generate any combination of differentiated cells even at their final division, indicating that intermediate precursors do not exist. In other regions of the central nervous system, in contrast, retroviral labeling studies have suggested the existence of lineage-restricted precursors that generate only one type of cell or a limited number of cell types. Intermediate stage precursors such as the bipotential oligodendrocyte-type-2-astrocyte precursor (O-2A) and a neuronal precursor have also been described in tissue culture studies. Yet, the generation of intermediate lineage-restricted precursors from pluripotent embryonic or adult stem cells or other stem cells capable of differentiating into neurons and glia had not been observed until recently, i.e. U.S. patent application Ser. No. 08/909,435, filed Jul. 4, 1997. Thus, the lineal relationship between pluripotent stem cells identified in culture and the committed precursors identified in vivo and in vitro had heretofore been unknown. Possible models of development have included (1) pluripotent and more committed stem cells representing lineally related cells or (2) such cells representing independent pathways of differentiation.

The developing rat spinal cord represents an ideal model for studying this differentiation. At embryonic day 10.5 (E10.5), the caudal neural tube appears as a homogeneous population of nestin-immunoreactive dividing cells in vivo and in vitro. These initially homogeneous cells are patterned over several days to generate neurons, oligodendrocytes, and astrocytes in a characteristic spatial and temporal profile. Neurogenesis occurs first on a ventro-dorsal gradient, with the earliest neurons becoming postmitotic on E13.5 in rats. Neurogenesis continues over an additional two days followed by differentiation of oligodendrocyte precursors and the subsequent differentiation of astrocytes.

Methods for growing neuroepithelial stem (NEP) cells isolated from E10.5 rat embryos as undifferentiated cells for extended periods in vitro have been described in Ser. No. 08/852,744, and it has been shown further that these populations were able to generate the three major cells types in the CNS. Thus, NEP cells represent a dividing multipotent stem cell that may differentiate into neurons either via an intermediate neuroblast or directly as a part of its terminal differentiation. To determine whether neurons differentiated from NEP cells via intermediate, more-restricted precursors, a variety of immunologically defined populations from differentiating cultures of NEP cells were isolated and characterized. It is shown herein that cells morphologically and phenotypically identical to NRP's can be isolated from NEP cell cultures. Clonal analysis shows that individual NEP cells generate neurons via the generation of neuronal precursors and that individual NEP cells can generate neuron-restricted and glial-restricted precursors. It is further shown that E-NCAM$^+$ (embryonic neural cell adhesion molecule positive) cells are present in E13.5 neural tube cultures and that these cells are mitotic, self renewing stem cells that can generate multiple neuronal phenotypes, but not astrocytes or oligodendrocytes. Thus, neuron restricted precursors (NRPs) are an identifiable stage in the in vivo differentiation of neurons. Moreover, it is shown that NRPs can be isolated and cultured from mouse embryos, mouse embryonic stem (ES) cells, and from human embryonic spinal cords. These data provide a demonstration of a direct lineal relationship between multipotent and neuron-restricted stem cells and suggest that neural differentiation involves progressive restriction in developmental fate.

FIG. 1 presents a model for spinal cord differentiation. This model is similar to that proposed for hematopoiesis and for differentiation of neural crest (see review by D. J. Anderson, The Neural Crest Lineage Problem: Neuropoiesis?, 3 Neuron 1–12 (1989)). According to this model, NEP cells 10 represent a homogeneous population of cells in the caudal neural tube that express nestin (i.e. nestin$^+$) but no other lineage marker (lin$^-$). These cells divide and self renew in culture and generate differentiated phenotypes. Previous data have suggested intermediate dividing precursors with a more restricted potential. Such precursors include glial restricted precursors 14 that generate oligodendrocytes 18 and astrocytes 22, as well as neuronal progenitors 26 that generate several kinds of neurons 30, 34. The model also shows that neural crest stem cells 38, which can differentiate into PNS neurons 42, Schwann cells 46, and smooth muscle cells 50, also descend from NEP cells. The model therefore suggests that the multipotent precursors (NEP cells) generate differentiated cells (i.e., oligodendrocytes, type 2 astrocytes, type 1 astrocytes, neurons, motoneurons, PNS neurons, Schwann cells, and smooth muscle cells) through intermediate precursors. Consistent with this model are the results presented herein showing the existence of cells with a neuron-restricted proliferative potential.

NEP cell cultures provide a large source of transient cells that can be sorted to obtain differentiated cell types. The results described herein provide direct evidence to support a model describing initially multipotent cells undergoing progressive restriction in developmental potential under extrinsic influence to generate the different phenotypes within the CNS. Evidence is provided that initially multipotent NEP cells generate neuron-restricted precursors in vitro and that such neuron-restricted precursors are also present in vivo. It is also shown that NRPs fulfill criteria of blast cells and that a direct lineal relationship between multipotent stem cells and more restricted NEP cells exists.

The results presented herein support that E-NCAM-immunoreactive cells are restricted in their developmental potential. E-NCAM$^+$ cells failed to differentiate into oligodendrocytes or astrocytes under any culture conditions tested. In contrast, NEP cells differentiated into neurons, astrocytes, and oligodendrocytes, and A2B5-immunoreactive cells differentiate into oligodendrocytes under identical conditions. For these reasons, E-NCAM-in-immunoreactive cells are described herein as neuron-restricted precursors or NRPs.

Immunopanning and double-labeling data demonstrate that E-NCAM can be used to identify a specific neuronal sublineage that is generated from multipotential NEP cells. Like markers for intermediate precursors in the hematopoietic system and neural crest, however, E-NCAM, and the A2B5 glial precursor marker as well, is not unique to intermediate precursors. E-NCAM has been shown to label some astrocytes. Similarly, A2B5 has been shown to recognize neurons in some species and is transiently expressed by astrocytes in some culture conditions. Nevertheless, under the specific culture conditions defined herein these markers can be used to select intermediate precursors and therefore represent the first cell surface epitopes that are co-expressed in concordance with a restriction in developmental potential.

The basal medium (NEP medium) used in the experiments described herein comprises DMEM-F12 (GIBCO/BRL, Gaithersburg, Md.) supplemented with 100 $\mu$g/ml transferrin (Calbiochem, San Diego, Calif.), 5 $\mu$g/ml insulin (Sigma Chemical Co., St. Louis, Mo.), 16 $\mu$g/ml putrescine (Sigma), 20 nM progesterone (Sigma), 30 nM selenious acid (Sigma), 1 mg/ml bovine serum albumin (GIBCO/BRL), plus B27 additives (GIBCO/BRL), 20 ng/ml basic fibroblast growth factor (bFGF), and 10% chick embryo extract (CEE). In general, these additives were stored as 100× concentrates at −20° C. until use. Normally, 200 ml of NEP medium was prepared with all additives except CEE and used within two weeks of preparation. CEE was added to the NEP medium at the time of feeding cultured cells.

FGF and CEE were prepared as described in D. L. Stemple & D. J. Anderson, supra; M. S. Rao & D. J. Anderson, supra; L. Sommers et al., Cellular Function of the bHLH Transcription Factor MASH1 in Mammalian Neurogenesis, 15 Neuron 1245–58 (1995), hereby incorporated by reference. FGF is also available commercially (UBI).

Briefly, CEE was prepared as follows. Chick eggs were incubated for 11 days at 38° C. in a humidified atmosphere. Eggs were washed and the embryos were removed and placed in a petri dish containing sterile Minimal Essential Medium (MEM with glutamine and Earle's salts) (GIBCO/BRL) at 4° C. Approximately 10 embryos each were macerated by passage through a 30-ml syringe into a 50-ml test tube. This procedure typically produced about 25 ml of medium. To each 25 ml was added 25 ml of MEM. The tubes were rocked at 4° C. for 1 hour. Sterile hyaluronidase (1 mg/25 g of embryo) (Sigma) was added, and the mixture was centrifuged for 6 hours at 30,000 g. The supernate was collected, passed through a 0.45 $\mu$m filter and then through a 0.22 $\mu$m filter, and stored at −80° C. until use.

Laminin (Biomedical Technologies Inc.) was dissolved in distilled water to a concentration of 20 mg/ml and applied to tissue culture plates (Falcon). Fibronectin (Sigma) was resuspended to a stock concentration of 10 mg/ml and stored at −80° C. and then diluted to a concentration of 250 $\mu$g/ml in D-PBS (GIBCO/BRL). The fibronectin solution was applied to tissue culture dishes and immediately withdrawn. Subsequently, the laminin solution was applied and plates were incubated for 5 hours. Excess laminin was withdrawn, and the plates were allowed to air dry. Coated plates were then rinsed with water and allowed to dry again. Fibronectin was chosen as a growth substrate for NEP cells because NEP cells did not adhere to collagen or poly-L-lysine (PLL) and adhered poorly to laminin. Thus, all subsequent experiments to maintain NEP cells in culture were performed on fibronectin-coated dishes. Laminin-coated dishes were used, however, to promote differentiation of NEP stem cells.

For clonal analysis, cells harvested by trypsinization were plated at a density of 50–100 cells per 35 mm dish. Individual cells were identified and located on the dish by marking the position with a grease pencil. Cells were grown in DMEM/F12 with additives, as described above, for a period ranging from 10–15 days.

The cells of the present invention may be used in the preparation of compositions, including pharmaceutical compositions, which may be appropriately formulated and administered to treat and correct deficiencies, debilitations, and other dysfunctions that may result from injury, disease, or other degeneration of relevant neural tissue. By way of non-limiting examples, suitable cells prepared in accordance with the present invention may be administered, e.g., by implantation as a means of effecting cell-replacement therapy, to treat instances where cell injury or debilitation has taken place. Thus, for example, the cells may be prepared in appropriate growth medium such as one for promotion of growth and differentiation. Suitable medium may include, for example, growth or differentiation factors, e.g., retinoic acid, BMP-2, BMP-4, or one or more members of the neurotrophins such as NT-3, NT-4, CNTF, BDNF and the like. Cells thus suitably prepared in such medium would be introduced either intrathecally, I.V., I.P., or wherever or by any means by which introduction of the cell preparation to the target site is best accomplished. The particulars of administration of this type may vary and would be within the skill set of the physician or practitioner.

The cells of the present invention are likewise useful in a variety of diagnostic applications and may, for example, be prepared for use in a screening assay, e.g., for identification of neuronal markers and other binding partners or ligands, modulators or other factors that may function as modulators of cell growth and/or differentiation. The cells of the present invention may also be used, e.g., as a positive control in an assay to identify deficiencies in cell growth and differentiation, and the factors that may be the cause thereof.

The cells of the present invention may be utilized in a variety of therapeutic applications, including in the preparation of pharmaceutical compositions and appropriate carriers, for administration to individuals in need of such therapy, to treat various cellular debilitation, dysfunctions or other irregularities or abnormalities associated with injury, disease or genetically caused neuronal deficits. Maladies or conditions contemplated herein include Parkinson's disease, Huntington's disease, Alzheimer's disease, dysfunctions resulting from injury or trauma, amyotrophic lateral sclerosis (ALS or Lou Gehrig's Disease), and anencephaly.

needles, rinsed, and then transferred to fresh HBSS. Spinal cords were mechanically dissected free from the surrounding connective tissue using sharpened No. 5 forceps. Isolated spinal cords were incubated in 0.05% trypsin/EDTA solution for 20 minutes.

TABLE 1

| Antibody/Kind | Source | Antigen Recognized | Cell Type Recognized |
|---|---|---|---|
| Anti-NCAM/mouse IgG | DSHB[a] | Polysialated-CAM | Neurons |
| Anti-Nestin | DSHB | Nestin | NEP cells |
| Anti-β-III tubulin/mouse IgG1 | Sigma[b] | Intermediate filament | Neurons |
| RT-97 | DSHB | Neurofilaments | Neurons |
| Anti-A2B5/mouse IgM | BMB[c] | Ganglioside | Oligodendrocytes and precursors |
| Anti-GFAP/rabbit IgG | Accurate[d] | Glial fibrillary acid | Astrocytes |
| Anti-NF60 | Chemicon[e] | Neurofilament 60 | Neurons |
| Anti-GalC/mouse IgG | BMB | Galactocerebroside | Oligodendrocytes and precursors |
| Anti-Peripherin | Chemicon | Peripherin | Motoneurons, PNS Neurons |
| Anti-MAP kinase | Chemicon | MAP2 kinase | Neurons |

[a]Developmental Studies Hybridoma Bank, Iowa
[b]Sigma Chemical Co., St. Louis, MO
[c]Boehringer Mannheim Biochemicals, Gaithersburg, MD
[d]Accurate, Westbury, NY
[e]Chemicon, Temecula, CA

EXAMPLE 1

To determine if a dividing neuron-restricted precursor is normally present in vivo, sections of E13.5 rat spinal cords were analyzed with a panel of early neuronal markers. Sections were cut of embryos fresh frozen at 13.5 days gestation and then were labeled by immunocytochemistry. Staining procedures were carried out according to methods well known in the art. Cells were double-labeled with antibodies against E-NCAM (Developmental Studies Hybridoma Bank, Iowa) and β-III tubulin (Sigma Chemical Co., St. Louis, Mo.) or were stained with E-NCAM and counterstained with DAPI, a nuclear marker for identifying all cells. All secondary monoclonal antibodies were from Southern Biotechnology.

Polysialated or embryonic N-CAM (E-NCAM) appeared to be a likely marker for neuronal precursors. E-NCAM immunoreactivity was first detected at E13.5. E-NCAM immunoreactive cells could be seen in the margins of the neural tube, but not in the proliferating ventricular zone. Double-labeling with β-III tubulin indicated that most E-NCAM-immunoreactive cells co-expressed this neuronal marker. A small proportion of cells present more medially were E-NCAM$^+$, but did not express β-III tubulin immunoreactivity, suggesting that E-NCAM may be an early and specific marker of differentiation into neuronal precursors that is expressed prior to β-III tubulin.

EXAMPLE 2

To characterize E-NCAM-immunoreactive cells, E13.5 spinal cords were dissociated and E-NCAM-immunoreactive cells were stained with a panel of antibodies (Table 1). Sprague-Dawley rat embryos were removed at embryonic day 13.5 and placed in a petri dish containing Hanks balanced salt solutions (HBSS, Gibco). The trunk segments of the embryos were dissected using tungsten needles, rinsed, and then transferred to fresh HBSS. Spinal cords were mechanically dissected free from the surrounding connective tissue using sharpened No. 5 forceps. Isolated spinal cords were incubated in 0.05% trypsin/EDTA solution for 20 minutes.

The trypsin solution was replaced with fresh HBSS containing 10% fetal bovine serum (FBS). The segments were gently triturated with a Pasteur pipette to dissociate cells. Cells dissociated by trituration were plated in PLL/laminin-coated 35 mm dishes (Nunc) at high density and stained after 24 hours.

Staining for the cell surface markers, such as A2B5 and α-GalC, was carried out with cultures of living cells. To stain cells with antibodies against internal antigens such as GFAP, which specifically recognizes astrocytes (A. Bignami et al., Localization of the Glial Fibrillary Acidic Protein in Astrocytes, by Immunofluorescence, 43 Brain Res. 429–35 (1972)), β-III tubulin (DAKO) and RT-97, which stain neurons (E. Geisert & A. Frankfurter, The Neuronal Response to Injury as Visualized by Immunostaining of Class β-tubulin in the Rat, 102 Neurosci. Lett. 137–41 (1989), nestin, which is a marker for undifferentiated stem cells (U. Lendahl et al., CNS Stem Cells Express a New Class of Intermediate Filament Protein, 60 Cell 585–95 (1990)), or 5-bromodeoxyuridine (BrdU, Sigma), which is a marker for determining the number of dividing cells, cultures were fixed in ice-cold methanol. Double- or triple-labeling experiments were performed by simultaneously incubating cells in appropriate combinations of primary antibodies followed by non-cross-reactive secondary antibodies, e.g. M. Mayer et al., Ciliary Neurotrophic Factor and Leukemia Inhibitory Factor Promote the Generation, Maturation, and Survival of Oligodendrocytes, 120 Development 142–53 (1994), hereby incorporated by reference. In triple-label experiments, cultures were incubated with the primary antibody in blocking buffer for a period of 1 hour, rinsed with PBS, and incubated with a species-specific secondary antibody in blocking buffer for 1 hour. Cultures were rinsed three times with PBS and examined under a fluorescence microscope. For labeling with 4 antibodies simultaneously, live cells were first incubated with the surface antibodies A2B5 and α-GalC without the secondary layers. Cells were then fixed in ice-cold methanol for ten minutes and stained with α-β-III tubulin and the appropriate secondary antibody. After scoring the results of this staining, which was usually negative, clones were stained with GFAP and the secondary layer for the first set of surface antibodies. Finally, the secondary antibody for GFAP was added. This procedure allowed staining with four antibodies using only three fluorescent-color conjugated secondary antibodies.

E-NCAM-immunoreactive cells constituted 60%±3% of all cells present in dissociated culture 24 hours after plating. The majority of the remaining cells were A2B5+. It has been shown in U.S. patent application Ser. No. 08/852,744 that at this stage of development, A2B5-immunoreactive cells are glial precursor cells. Consistent with these results, β-III tubulin or E-NCAM-immunoreactive cells did not coxpress A2B5. The vast majority of cultured E-NCAM-immunoreactive cells (85%±8%) co-expressed β-III tubulin immunoreactivity as well as nestin immunoreactivity, but not markers characteristic of glial precursor immunoreactivity. Approximately 20% of the E-NCAM+ cells divided in a 24-hour period. Most of the dividing E-NCAM+ cells did not co-express β-III tubulin, indicating that this population of cells could represent a dividing neuroblast. It is not yet known whether a higher percentage of the cells would be observed to divide under these conditions with longer labeling periods. However, even if this population were to include a subset of cells sufficiently committed to neuronal differentiation as to no longer engage in division, these committed neurons would be eliminated from the population with expansion and division in tissue culture. Table 2 summarizes results of the antigenic profile of the cells, showing the percentages of E-NCAM+ cells from E13.5 embryos that express various other antigens. These results show that E-NCAM+ cells from E13.5 spinal cord express neuronal, but not glial, markers.

TABLE 2

| Antigen | % Expression |
| --- | --- |
| α-Nestin | 98% |
| α-β-III-tubulin | 50% |
| RT-97 | 95% |
| α-NF M | 100% |
| α-MAP kinase | 100% |
| A2B5 | 0% |
| α-GFAP | 0% |
| α-NF 60 | 0% |
| αGalC | 0% |
| α-Peripherin | 0% |

EXAMPLE 3

To determine the differentiation potential of E-NCAM-immunoreactive cells, E-NCAM+ cells were purified by immunopanning and plated at clonal density in gridded dishes. E13.5 cells were prepared according to the procedure of Example 2. An E-NCAM+ cell population was purified from these E13.5 cells using a specific antibody-capture technique according to the procedure of L. Wysocki & V. Sato, "Panning" for Lymphocytes: A Method for Cell Selection, Proc. Nat'l Acad. Sci. USA 2844–48 (1978); M. Mayer et al., supra, hereby incorporated by reference. In brief, cells were trypsinized and the resulting cell suspension was plated on an A2B5-antibody-coated dish to allow binding of all A2B5+ cells to the plate. The supernate was removed, and the plate was washed with DMEM supplemented with additives described by J. Bottenstein and G. Sato, Growth of a Rat Neuroblastoma Cell Line in Serum-free Supplemented Medium, 76 Proc. Nat'l Acad. Sci. USA 514–17 (1979), hereby incorporated by reference, (DMEM-BS). The supernate was then plated on an E-NCAM-antibody-coated dish to allow binding of the E-NCAM-immunoreactive cells. The bound cells were scraped from the plate and replated on fibronectin/laminin-coated glass coverslips in 300 ml DMEM-BS±growth factors at 5000 cells/well.

The A2B5 and E-NCAM antibodies for coating the plates were used at concentrations of 5 µg/ml. Cells were allowed to bind to the plate for 20–30 minutes in a 37° C. incubator. Growth factors were added every other day at a concentration of 10 ng/ml. Recombinant bFGF and neurotrophin 3 (NT-3) were purchased from PeproTech, and retinoic acid (RA) was obtained from Sigma.

After 24 hours, some immunopanned E-NCAM+ cells were assayed by immunocytochemistry according to the procedure of Example 2. Greater than 95% of the cells were E-NCAM+ at that time. Purified and stained cells were plated on gridded clonal dishes, and individual E-NCAM+ cells were identified and followed over time by immunocytochemistry according to the procedure of Example 2.

Of all the cytokines tested, optimum growth was observed when cells were cultured in FGF (10 ng/ml) and NT-3 (10 ng/ml). In the presence of FGF and NT-3, single E-NCAM+ cells divided in culture to generate colonies ranging from one to several hundred cells. By day 5, most colonies contained between 20 and 50 daughter cells that continued to express E-NCAM immunoreactivity. Daughter cells appeared phase bright and had short processes. At this stage, most E-NCAM-positive cells did not express β-III tubulin or neurofilament-M immunoreactivity.

To promote differentiation of E-NCAM+ clones, the FGF- and NT-3-containing medium was replaced with medium containing retinoic acid (RA) and from which the mitogen, bFGF, was withheld. In this differentiation medium, E-NCAM+ cells stopped dividing and elaborated extensive processes and started to express neuronal markers. Quadruple-labeling of clones with neuronal and glial markers and DAPI histochemistry, to identify all cells, showed that all clones contained β-III tubulin-immunoreactive cells and neurofilament-M (NF-M) immunoreactive cells and that none of the E-NCAM+ clones differentiated into oligodendrocytes or astrocytes.

Table 3 summarizes the results obtained by quadruple labeling of 124 E-NCAM+ clones with DAPI, α-β-III tubulin, A2B5, and α-GFAP.

TABLE 3

| Antigen Expressed | % of Clones |
| --- | --- |
| α-β-III tubulin | 100% |
| A2B5 | 0% |
| α-GFAP | 0% |

EXAMPLE 4

In this example, immunopanned A2B5+ cells derived from dissociated E13.5 spinal cords according to the procedure of Example 2 were cultured in neuron-promoting medium, i.e. basal medium plus FGF and NT-3. Cultures were grown for 5 days and then switched to RA-containing medium as described in Example 3, and sister plates were stained for either E-NCAM or A2B5 immunoreactivity.

No A2B5 immunopanned cell expressed E-NCAM immunoreactivity when grown under conditions that promote growth of neuronal cells. All A2B5 immunopanned cells, however, continued to express A2B5 immunoreactivity, indicating that neuron-promoting conditions do not affect the survival and proliferation of glial precursor cells. Thus, the inability to detect oligodendrocyte and astrocyte differentiation in Example 3 was unlikely to be due to the death in neuronal cultures of oligodendrocytes and astrocytes that might have differentiated from E-NCAM+ precursors since A2B5 glial precursor cells purified and grown in parallel in the presence of FGF and NT-3 continued to express A2B5 without apparent cell death and generated healthy oligodendrocytes and astrocytes after 10 days in culture. In addition, A2B5$^+$ cells never generated neurons in the presence of FGF and NT-3 and showed no expression of E-NCAM at any time tested. Thus, E-NCAM immunoreactive cells, unlike A2B5-immunoreactive glial restricted precursors, could not differentiate into oligodendrocytes and appeared limited to neuronal differentiation when compared to multipotential E10.5 neuroepithelial cells.

EXAMPLE 5

While it has been clearly shown in the present system that E-NCAM identifies neuronally restricted precursor cells, it has been reported that certain glial precursors at later stages of development can also express E-NCAM immunoreactivity. This observation raises the possibility that some E-NCAM$^+$ cells identified by the presently described methods may be bi-potential. To test this possibility, E-NCAM$^+$ cells were plated clonally in either neuron-promoting medium (FGF+NT-3) or in glial-promoting medium (FGF+ 10% fetal calf serum) and compared for their development. Medium containing FGF with 10% fetal calf serum was chosen for glial differentiation since this medium promotes astrocyte differentiation of both spinal cord NEP cells as well as A2B5 immunoreactive A2B5 glial precursor cells, as shown in U.S. patent application Ser. No. 08/852,744. All E-NCAM$^+$ clones (24/24) that were grown in neuron-promoting medium contained only β-III tubulin$^+$ cells after 8 days, while the clones grown in serum-containing medium did not generate astrocytes or proliferate. From a total of 97 E-NCAM$^+$ cells grown in glial-promoting conditions, 90 clones (92%) consisted of a single dead cell after 24 hours, while the remaining 7 clones (8%) contained 1 or 2 dead cells after 48 hours. Thus, E-NCAM immunoreactive cells, in contrast with glial precursor cells, fail to proliferate or differentiate in astrocyte-promoting conditions.

EXAMPLE 6

To determine whether the restriction of E-NCAM$^+$ cells to generation of neurons also includes a restriction to generation of certain subtypes of neurons, E-NCAM$^+$ clones grown in RA and NT-3 in the absence of FGF were examined for the expression of different neurotransmitters. The antibodies used in this example are described in Table 4.

TABLE 4

| Antibody/Kind | Source | Antigen Recognized | Cell Type Recognized |
|---|---|---|---|
| Anti-ChAT/goat IgG | Chemicon | Choline acetyl transferase | Motoneurons |
| Anti-Glutamate/rabbit IgG | Chemicon | Glutamate | Excitatory neurons |
| Anti-GABA/rabbit IgG | Chemicon | Gamma amino butyric acid | Inhibitory neurons |

These results indicate that individual clones could generate GABA-ergic, glutaminergic, and cholinergic neurons. Of ten clones tested, all contained glutarinergic, GABAergic, and cholinergic neurons. Thus, E-NCAM-immunoreactive cells, while limited to differentiating neurons, are capable of generating excitatory, inhibitory, and cholinergic neurons.

EXAMPLE 7

Primary clones of E-NCAM$^+$ cells grown in FGF and NT-3 according to the procedure of Example 5 grew to large sizes of several hundred cells after 7 to 10 days in culture, indicating some degree of self renewal. To demonstrate prolonged self renewal of the E-NCAM$^+$ population, selected clones were followed by secondary and tertiary subcloning. Individual E-NCAM$^+$ cells from E13.5 spinal cord were plated in fibronectin/laminin and expanded for 7 days in the presence of FGF and NT-3. Five individual clones were randomly selected and replated at clonal density using the same expansion conditions. The number of secondary clones was counted, and large clones were selected and replated. The number of tertiary clones obtained was counted, and clones were then induced to differentiate into postmitotic neurons by replacing FGF and RA.

All clones examined generated numerous daughter clones that subsequently generated tertiary clones. Small clones and very large clones showed similar self renewal potential. When tertiary clones were switched to a medium containing RA and lacking FGF, the majority of cells in a clone differentiated into post-mitotic neurons expressing β-III tubulin. Thus, E-NCAM$^+$ cells are capable of prolonged self renewal and can generate multiple daughter cells capable of generating neurons.

These results suggest that E-NCAM immunoreactivity identifies a neuroblast cell that can differentiate into multiple neuronal phenotypes in culture, even after multiple passages. NT-3 and FGF are required to maintain the blast cell in a proliferative state, while RA promotes differentiation.

EXAMPLE 8

It has been shown previously that individual NEP cells derived from E10.5 spinal cord are an E-NCAM-immunonegative, multipotent, self renewing population of cells that can generate neurons, astrocytes, and oligodendrocytes (U.S. patent application Ser. No. 08/852,744). To determine if neuronal differentiation from NEP precursors involved the generation of an E-NCAM$^+$ intermediate neuronal precursor cell, NEP cell cultures that were induced to differentiate in vitro were examined for the presence of E-NCAM$^+$ immunoreactive cells.

NEP cells were prepared according to the method described in Ser. No. 08/852,744. Briefly, Sprague Dawley rat embryos were removed at E10.5 (13–22 somites) and placed in a petri dish containing Ca/Mg-free Hanks balanced salt solution (HBSS, GIBCO/BRL). The trunk segments of the embryos (last 10 somites) were dissected using tungsten needles, rinsed, and then transferred to fresh HBSS. Trunk segments were incubated at 4° C. in 1% trypsin solution (GIBCO/BRL) for a period of ten to twelve minutes. The trypsin solution was replaced with fresh HBSS containing 10% fetal bovine serum (FBS, GIBCO/BRL). The segments were gently triturated with a Pasteur pipette to release neural tubes free from surrounding somites and connective tissue. Isolated neural tubes were transferred to a 0.05% trypsin/ EDTA solution (GIBCO/BRL) for an additional period of ten minutes. Cells were dissociated by trituration and plated at high density in 35 mm fibronectin-coated dishes in NEP medium. Cells were maintained at 37° C. in 5% CO$_2$/95% air. Cells were replated at low density, i.e. ≦5000 cells per 35 mm plate, one to three days after plating. Cells from several dishes were then harvested by trypsinization (0.05% trypsin/EDTA solution for two minutes). Cells were then pelleted, resuspended in a small volume, and counted. About 5000 cells were plated in a 35 mm dish (Corning or Nunc).

NEP cells derived from E10.5 embryos were expanded in the presence of FGF and CEE for 5 days and differentiated by replating on laminin in the presence of CEE. Differentiating NEP cells were triple-labeled with antibodies to E-NCAM, GFAP, and GalC. This showed that E-NCAM-immunoreactive cells that differentiated from NEP cells did not express astrocytic (GFAP) or oligodendrocytic (GalC) markers. A sister plate was double-labeled with antibodies to E-NCAM and nestin. This showed that E-NCAM immunoreactive cells that differentiated from NEP cells co-express nestin. Differentiating NEP cells were incubated for 24 hours with BrdU and subsequently double-labeled with an antibody against BrdU and E-NCAM. This showed that most E-NCAM-immunoreactive cells divided in 24 hours. This higher labeling rate may reflect differences in the isolate procedure as compared to the previous example. Table 5 summarizes the antigenic profile of E-NCAM$^+$ cells derived from E10.5 NEP cells. Note that NEP-derived E-NCAM$^+$ cells are antigenically similar to E13.5 E-NCAM$^+$ cells and, like E13.5 E-NCAM$^+$, do not express any of the glial markers examined.

TABLE 5

| Antigen | Expression |
| --- | --- |
| α-Nestin | +/− |
| α-β-III tubulin* | + |
| A2B5 | − |
| α-GFAP | − |
| α-GalC | − |

*A subset of cells express this marker.

Thus, induced NEP cultures comprise multiple phenotypes, including E-NCAM$^+$ cells. Like the E13.5 E-NCAM$^+$ cells, NEP-derived E-NCAM$^+$ cells did not express glial markers, but co-expressed β-III tubulin (20–30%) and nestin (70–80%) immunoreactivity. Ninety percent of panned E-NCAM$^+$ cells incorporated BrdU in culture and generated neurons after addition of RA or NT-3 and thus appeared similar to the E13.5 E-NCAM-immunoreactive cells.

EXAMPLE 9

To determine whether single NEP-derived E-NCAM$^+$ cells were also restricted to neurons in their differentiation potential, cells were studied in clonal culture. NEP cells were induced to differentiate by replating on laminin and withdrawal of CEE, as described in U.S. patent application Ser. No. 08/852,744. NEP cells derived from E10.5 embryos were expanded in the presence of FGF and CEE for 5 days and differentiated by replating on laminin in the absence of CEE. Immunopanned E-NCAM-immunoreactive cells were then plated on clonal-grid dishes (Greiner Labortechnik) coated with fibronectin/laminin, and single cells were followed in culture. After 5 days, clones were switched to RA and FGF was withdrawn. Clones were allowed to grow for an additional 3 days, fixed with paraformaldehyde, and triple-labeled with A2B5 and antibodies against GFAP and β-III tubulin. In addition, cells were counterstained with DAPI to show individual cell nuclei. Table 6 summarizes the results of the staining of all 47 clones studied (8 of 47 clones did not survive replating). Note that no clone contained astrocytes (GFAP$^+$) cells or glial precursor cells (A2B5$^+$).

TABLE 6

| Antigen Expressed | % of Clones |
| --- | --- |
| α-β-III tubulin | 100% |
| A2B5 | 0% |
| α-GFAP | 0% |

Forty-eight hours after cells were induced to differentiate, 10–30% of the cells had begun to express E-NCAM immunoreactivity. NEP-cell-derived E-NCAM$^+$ cells were selected by immunopanning according to the procedure of Example 3, and individual E-NCAM$^+$ cells were plated in medium containing FGF and NT-3 and clones were analyzed after 10 days.

All clones contained only E-NCAM$^+$/β-III tubulin$^+$ cells, but not GFAP or A2B5 immunoreactive cells. In addition, individual E-NCAM$^+$ cells failed to differentiate into oligodendrocytes or astrocytes under culture conditions that promoted astrocytic and oligodendroglial differentiation from the parent NEP cell population. E-NCAM$^+$ cells could be maintained as dividing precursor cells in defined medium in the presence of high concentrations of FGF (10 ng/ml) and NT-3 (10 ng/ml). E-NCAM$^+$ cells maintained for up to three months could readily differentiate into β-III tubulin$^+$ mature neurons that expressed a variety of neurotransmitter phenotypes when exposed to RA grown on laminin. Thus, E-NCAM$^+$ cells are similar to E13.5 neuronal precursors in their differentiation potential, antigenic profile, and in the conditions optimal for extended growth as a dividing precursor cell population.

EXAMPLE 10

Differentiation of the E-NCAM$^+$ population from an apparently homogeneous Nestin$^+$/E-NCAM$^-$ NEP cell population suggests a progressive restriction in developmental fate. It was thought possible, but unlikely, that individual NEP cells could be pre-committed to generating neuroblasts or glioblasts. To rule out this possibility, individual NEP clones were examined for their ability to generate E-NCAM-immunoreactive cells and A2B5-immunoreactive cells. A2B5 and E-NCAM were chosen since it had previously been shown that A2B5 immunoreactivity is unique to oligodendrocyte-astrocyte precursors at this stage of development. NEP cells derived from E10.5 embryos were expanded in the presence of FGF and CEE for 5 days, harvested by trypsinization, and replated at clonal density in gridded clonal dishes. After 7 days in culture, individual clones were double-labeled with antibodies against E-NCAM and A2B5 according to the procedure of Example 2. Of 112 NEP clones that were followed in culture, 83% generated both A2B5 and E-NCAM immunoreactive cells. Five percent of the clones consisted of only A2B5 immunoreactive cells, and 12% of the clones showed no convincing staining for either A2B5 or E-NCAM immunoreactivity. In all clones tested, E-NCAM and A2B5 were expressed in non-overlapping populations. That is, no cell co-expressed both markers. Table 7 summarizes the results obtained with 112 clones.

TABLE 7

| Antigen Expressed | % of Clones | Number of Clones |
| --- | --- | --- |
| E-NCAM$^+$/A2B5$^+$ | 83% | 93 |
| A2B5$^+$ alone | 5% | 6 |
| E-NCAM$^-$/A2B5$^-$ | 12% | 13 |

Thus, the majority of NEP cells appear to be capable of generating precursors for glial restricted cells as well as neuronal restricted precursors.

EXAMPLE 11

To test if most neurons were generated via an E-NCAM$^+$ intermediate neuroblast, complement-mediated cell lysis was utilized to selectively kill E-NCAM$^+$ cells. Twenty-four hours after replating NEP cells in differentiating conditions, E-NCAM-immunoreactive cells were killed using an IgM antibody to E-NCAM and guinea pig complement. In sister plates, glial precursors were killed using an anti-A2B5 IgM antibody and complement. At this stage in development, most E-NCAM$^+$ cells do not express β-III tubulin. Treated plates were allowed to differentiate for an additional three days, and the development of neurons was monitored. E-NCAM-mediated lysis significantly reduced the number of β-III tubulin-immunoreactive cells that developed when compared to cultures treated with A2B5 (219±35 versus 879±63, respectively) suggesting that neuronal differentiation from NEP cells in vitro requires a transition through an E-NCAM immunoreactive state.

EXAMPLE 12

Differentiated E-NCAM$^+$ Cells can be Distinguished from Acutely Dissociated NRP Cells ENCAM$^+$ cells were isolated by immunopanning according to the procedure of Example 3, plated in 35 mm dishes, and allowed to grow for 24 hours (acutely dissociated) or 10 days (differentiated). Cultured cells were then analyzed for cell division by BRDU incorporation, E-NCAM expression, NF-M expression, and synaptophysin expression according to the procedure of Example 2. About 70% of acutely dissociated E-NCAM$^+$ cells incorporated BRDU, showing that such cells were dividing in culture, whereas after 10 days in differentiation promoting medium few or no cells incorporated BRDU, and had therefore stopped dividing. Double-labeling for E-NCAM and NF-M immunoreactivity showed that very few acutely dissociated cells expressed NF-M, whereas nearly all differentiated cells expressed this protein. Similarly, synaptophysin, a protein specifically associated with synaptic vesicles and functional synapses, see T. C. Sudhof, The Synaptic Vesicle Cycle: A Cascade of Protein-Protein Interactions, 375 Nature 645–653 (1995), was expressed by differentiated but not acutely dissociated ENCAM$^+$ cells. Although synaptophysin protein expression was associated with synaptic vesicles, early expression could also be detected in the cell bodies and throughout the lengths of the processes where it was initially expressed during neurogenesis. M. Fujita et al., Developmental Profiles of Synaptophysin in Granule Cells of Rat Cerebellum: An Immunocytochemical Study, 45 J. Electron Microsc. Tokyo 185–194 (1996); D. Grabs et al., Differential Expression of Synaptophysin and Synaptoporin during Pre- and Postnatal Development of the Rat Hippocampal Network, 6 Eur. J. Neurosci. 1765–1771 (1994). These results show that acutely dissociated E-NCAM$^+$ cells are immature, dividing cells that mature in culture. These results suggest that if NRP cells are induced to differentiate by RA and the removal of mitogen, they acquire many morphological and immunological properties of mature neurons.

EXAMPLE 13

Numerous Neuronal Phenotypes can be Detected in Differentiated but not Acutely Dissociated E-NCAM$^+$ Cells It was shown above that NRP cells can differentiate into postmitotic neurons, but not into oligodendrocytes or astrocytes. To determine if NRPs can differentiate into all of the major neuronal phenotypes present in the spinal cord, or whether they are more limited in their differentiation potential, the expression of neurotransmitter synthesizing enzymes and cell type specific markers for mature neurons was examined after inducing NRPs to differentiate. In addition, the expression of p75, Q. Yan & E. J. Johnson, An Immunocytochemical Study of the Nerve Growth Factor Receptor in Developing Rats, 8 J. Neurosci. 3481–3498 (1988), and Islet-1, T. Tsuchida et al., Topographic Organization of Embryonic Motor Neurons Defined by Expression of LIM Homeobox Genes, 79 Cell 957–970 (1994), which are characteristic of motoneurons in the spinal cord, and calbindin, which is often co-expressed with GABA, C. Batini, Cerebellar Localization and Colocalization of GABA and Calcium Binding Protein-D28K, 128 Arch. Ital. Biol. 127–149 (1990), were examined.

E-NCAM$^+$ cells from E13.5 rat neural tube were isolated by immunopanning according to the procedure of Example 3, plated in 35 mm dishes, and cultured in differentiation-promoting medium. After 10 days in culture, total RNA was isolated from these cells and the ability to synthesize the neurotransmitters acetylcholine (Ach), GABA, and glutamate was assessed by the expression of their synthesizing enzymes by RT-PCR. Total RNA was isolated from cells or whole tissues by a modification of the guanidine isothiocyanate-phenol-chloroform extraction method (TRIZOL, Gibco/BRL). For cDNA synthesis, 1–5 μg of total RNA was used in a 20 μl reaction using SUPERSCRIPT II (Gibco/BRL), a modified Maloney murine leukemia virus reverse transcriptase (RT), and oligo(dT)$_{12-18}$ primers according to the Gibco/BRL protocol.

For PCR amplification of the cDNA, aliquots of cDNA, equivalent to 1/20 of the reverse transcriptase reaction, were used in a 50 μl reaction volume. PCR amplification was performed using ELONGASE polymerase (Gibco/BRL). Primer sequences and cycling temperatures used for PCR amplification of receptors are shown in Table 8. The reactions were run for 35 cycles, and a 10-minute incubation at 72° C. was added at the end to ensure complete extension. The PCR products were purified using the ADVANTAGE PCR-PURE kit (Clontech, Palo Alto, Calif.) and sequenced to confirm their identities.

TABLE 8

| Gene | Product Size (bp) | Primers (sense, antisense) |
|---|---|---|
| p75 | 329 | SEQ ID NOS:1 and 2 |
| ChAT | 377 | SEQ ID NOS:3 and 4 |
| Isl-1 | 350 | SEQ ID NOS:5 and 6 |
| GAD$_{65}$ | 327 | SEQ ID NOS:7 and 8 |
| calbindin28 | 276 | SEQ ID NOS:9 and 10 |
| glutaminase | 560 | SEQ ID NOS:11 and 12 |
| cyclophilin | 302 | SEQ ID NOS:13 and 14 |

Figure 2:
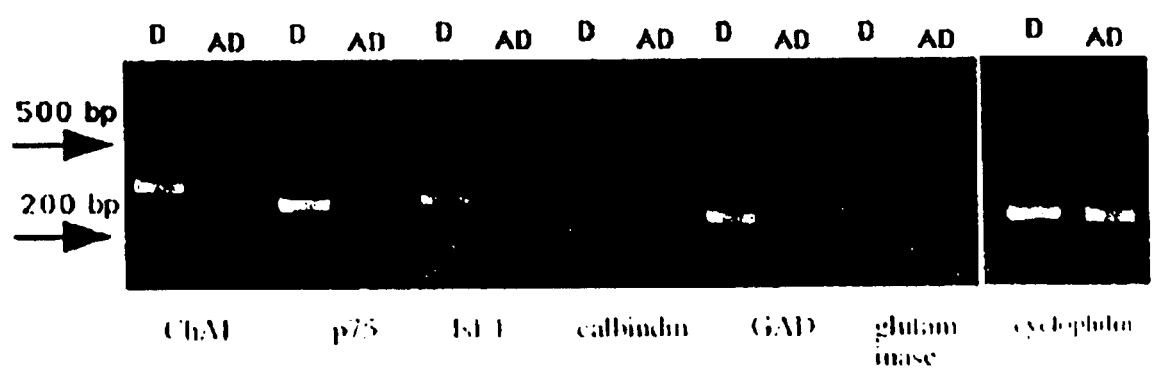
FIG. 2 shows results of RT-PCR amplification of total RNA isolated from rat E-NCAM$^+$ cells for determining expression of choline acetyl transferase (ChAT), p75, islet-1 (Isl-1), calbindin, glutamic acid decarboxylase (GAD), glutaminase, and cyclophilin (a housekeeping gene).

As shown in FIG. 2, all of these were present in differentiated cells (labeled "D"). In contrast, none of these markers of neurotransmitter phenotypes could be detected from cells that were examined within 24 hours of isolation (termed "acutely dissociated;" labeled as "AD" in FIG. 2), even though expression of the housekeeping gene, cyclophilin, could be readily detected from both cell populations. These data show that NRP cells mature in culture and that NCAM expression and neuronal fate determination precede neurotransmitter synthesis.

The expression of neurotransmitter synthesizing enzymes was also examined by immunocytochemistry to determine whether all cells, or only a subset of differentiated cells, express these markers. Cells were grown in culture for 10 days and allowed to differentiate, fixed, and processed by immunocytochemistry according to the procedure of Example 2 to detect expression of choline acetyltransferase (ChAT), glutamic acid decarboxylase (GAD), tyrosine hydroxylase (TH), glycine, and glutamate. Antibodies to ChAT, TH, and GAD were obtained from Chemicon; antibodies to glutamate and glycine were from Signature Immunologicals. Virtually 100% of the differentiated cells expressed detectable glutamate levels. A much smaller percentage expressed glycine and GAD. Exact percentages varied between experiments from 10–50%. The percentage of ChAT and TH$^+$ cells were even smaller and ranged between 1–5%. However, substantially larger numbers could be seen by altering culture conditions. Since virtually 100% of the cells synthesized glutamate, it is likely that at least some cells synthesized more than one neurotransmitter. Nevertheless, these results clearly show that upon differentiation, E-NCAM$^+$ cells are capable of maturing into a heterogeneous population with respect to their neurotransmitter phenotype.

In contrast to the results obtained with differentiated cells, neither ChAT, GAD, TH, nor glycine could be detected in acutely dissociated cells. Glutamate was detected in a small subset of such cells (less than 10%). Glutaminase, however, could not be detected in these cells by RT-PCR (FIG. 2), which suggests that glutamate was being taken up by these cells from the medium.

EXAMPLE 14

The Neurotransmitter Receptor Profile of E-NCAM$^+$ Cells Changes with Maturation Another important characteristic of mature neurons is their ability to respond to multiple neurotransmitters by expressing appropriate neurotransmitter receptors on their surfaces. To examine the ability of differentiated E-NCAM$^+$ cells to respond to glutamate, glycine, dopamine, and acetylcholine, fura-2 Ca$^{2+}$ imaging techniques were used. E13.5 E-NCAM$^+$ cells were grown in culture for 10 days and allowed to differentiate. They were then loaded with fura-2, and the depolarizing response to neurotransmitter application was monitored.

Cells were loaded with 5 $\mu$M Fura-2/AM, D. Grynkiewicz et al., A New Generation of Calcium Indicators with Greatly Improved Fluorescence Properties, 260 J. Biol. Chem. 3440–3450 (1985), hereby incorporated by reference, plus PLURONIC F127 (80 $\mu$g/ml) in rat ringers (RR) at 23° C. in the dark for 20 minutes followed by 3 washes in RR and a 30-minute desterification. Relative changes in intracellular calcium concentration were measured from the background-corrected ratio of fluorescence intensity by excitation at 340/380 nm. Response was defined as a minimum rise of 10% of the ratioed baseline value. A Zeiss-Attofluor imaging system and software (Atto Instruments Inc., Rockville, Md.) were used to acquire and analyze the data. Data points were sampled at 1 Hz. Neurotransmitters were made in RR and delivered by bath exchange using a small volume loop injector (200 $\mu$l). RR contained 140 mM NaCl, 3 mM KCl, 1 mM MgCl, 2 mM CaCl$_2$, 10 mM HEPES, and 10 mM glucose. In addition, 500 $\mu$M ascorbic acid was added to dopamine solutions to prevent oxidation. Control application of 500 $\mu$M ascorbic acid had no effect. The pH of all solutions was adjusted to 7.4 with NaOH. Further, 50 mM K$^+$ RR was made by substituting equimolar K$^+$ for Na$^+$ in the normal RR.

FIG. 3 shows a bar graph of the number of cells responding to application of the indicated neurotransmitter on acutely dissociated and differentiated cells. In general, the number of cells responding to neurotransmitters and the amplitude of the neurotransmitter-induced Ca$^{2+}$ responses increased in the differentiated cells. The most striking example was dopamine, where only 10% of the acutely dissociated cells responded to 500 $\mu$M dopamine with increases in internal Ca$^{2+}$ compared to 76% of differentiated cells, a net increase of 66%. Similar, but less striking, changes in the number of cells responding were seen for other excitatory neurotransmitters. The exceptions to this trend were the Ca$^{2+}$ responses to GABA and glycine. Interestingly, 46% of the acutely dissociated cells responded to GABA compared to only 8% of the differentiated cells. Similarly, Ca$^{2+}$ flux in response to glycine decreased from 20% in the acutely dissociated cells to 0% in the differentiated cells. This change in the inhibitory neurotransmitter profile probably reflects the decrease in internal chloride ion concentration with maturation that accounts for the shift from depolarizing to hyperpolarizing GABA and glycine responses. W. Wu et al., Early Development of Glycine and GABA-Mediated Synapses in Rat Spinal Cord, 12 J. Neurosci. 3935–3945 (1992). The possibility cannot be excluded, however, that chloride ion levels remain elevated and fewer GABA and glycine receptors are expressed in the differentiated cells. Representative plots of the ratio of ($I_{340}/I_{380}$) Ca$^{2+}$ responses over time from an acutely dissociated and differentiated cell are shown in FIG. 4 and FIG. 5, respectively. The acutely dissociated cell responded to GABA and glutamate, whereas the differentiated cell from the same embryo responded to dopamine, glutamate, and acetylcholine, but not to GABA or glycine. Comparison of Ca$^{2+}$ responses to the various transmitters in adjacent cells revealed that there is heterogeneity in the response profiles among cells, indicating that not only are the E-NCAM$^+$ cells heterogeneous in their ability to synthesize neurotransmitters, they are also selected in terms of transmitter receptor expression. In addition to neurotransmitters, elevated K$^+$ in rat ringers (50 mM K$^+$ RR) was applied to depolarize the cells and allow Ca$^{2+}$ entry through voltage-gated channels. In acutely dissociated cells, 49% responded to 50 mM K$^+$ RR compared to 85% of differentiated cells, suggesting that more of the differentiated cells were electrically competent than were the acutely dissociated cells.

Thus, the contrast between the various properties of acutely dissociated E-NCAM$^+$ cells and fully differentiated E-NCAM$^+$ cells, which are summarized in Table 9, is striking. Immature cells are mitotically active, but differentiated cells are not. Immature cells do not express any mature neuronal proteins such as NF-M, synaptophysin, or neurotransmitter synthetic enzymes, whereas all of these can be detected in differentiated cells. Moreover, acutely dissociated cells are overall less responsive than differentiated cells to neurotransmitter-induced Ca$^{2+}$ responses.

TABLE 9

| Property | Acutely Dissociated | Differentiated |
| --- | --- | --- |
| Mitotic Status | Mitotic | Postmitotic |
| Cell Size | Comparatively smaller | Comparatively larger |
| Process Outgrowth | Little or none | Extensive |
| Neuronal Markers | NCAM, βIII-tubulin, MAP-2 kinase, nestin | NCAM, βIII-tubulin, MAP-2 kinase, NF-M, synaptophysin, peripherin |
| Neurotransmitters, neurotransmitter synthetic enzymes, or other phenotypic specific markers | None, except for a small amount of glutamate immunoreactivity. | Glutamate, glycine, glutaminase, GAD, ChAT, Isl-1, p75, calbindin |
| Response to neurotransmitters | Weak, in a small subset of cells. | Robust and in virtually all cells. |

TABLE 9-continued

| Property | Acutely Dissociated | Differentiated |
| --- | --- | --- |
| Depolarizing response to GABA and glycine | All responses measured were depolarizing. | Few or no depolarizing responses were detected. |

EXAMPLE 15

Individual E-NCAM+ Cells can Generate Multiple Neurotransmitter Phenotypes

Mass culture experiments described above showed that the E-NCAM+ population can generate multiple neurotransmitter phenotypes. There existed the possibility, however, that individual cells could be pre-committed to generating specific neuronal phenotypes. To determine whether the differentiation potential of NRPs in mass culture reflected the potential of an individual NRP, clonal analysis of E-NCAM+ cells was performed. E-NCAM+ cells were immunoselected according to the procedure of Example 3, plated at clonal density, and grown in FGF and NT-3, conditions that promote proliferation. Clones grew to sizes of several hundred cells after 10 days in culture, after which their differentiation was promoted by withdrawal of FGF and addition of RA in the medium.

Figure 6:
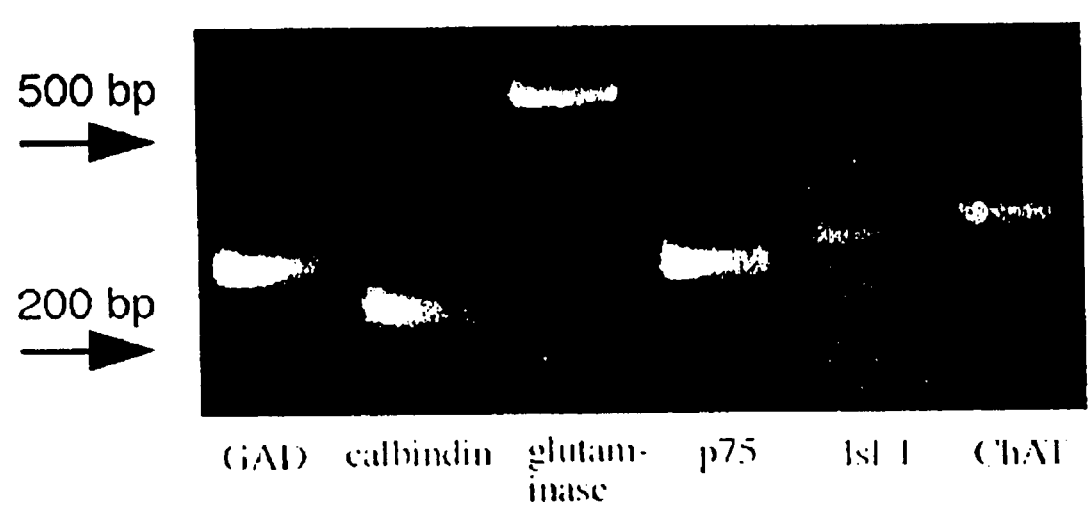
FIG. 6 shows the results of PCR analysis of a single E-NCAM$^+$ clone for expression of markers of mature neurons.

Three different techniques were used to determine whether clones generated from individual NRP cells were composed of heterogeneous populations of neurons: RT-PCR according to the procedure of Example 13, immunocytochemistry according to the procedure of Example 2, and calcium imaging according to the procedure of Example 14. Six clones were examined by RT-PRC analysis. Five of the six clones expressed multiple neurotransmitter phenotypes: one clone expressed all six markers tested, 3 clones expressed four markers, and 1 clone expressed three markers. Therefore, all but one clone were composed of heterogeneous populations of cells. One clone expressed detectable levels of only p75 and Isl-1, but not ChAT. This likely represented an immature clone that had not fully differentiated. FIG. 6 shows results from a representative clone that expressed all neurotransmitter markers tested. These results demonstrate that individual clones express multiple neurotransmitter synthetic enzymes or other phenotypic markers, and that most clones were composed of a heterogeneous population.

To confirm the PCR results and to show heterogeneity at the protein level, clones were analyzed for expression of p75. No clone (0/17) consisted of exclusively p75 immunoreactive cells, but all clones (17/17) contained p75 immunoreactive cells as well as other neurons. Similarly, staining for either glutamate or glycine immunoreactivity showed that each transmitter was expressed by only a subset of cells in the same clonal population, indicating that clones are a heterogeneous population.

Heterogeneity was demonstrated not only by the synthesis of different neurotransmitters, but also by heterogeneity in the receptors expressed by the cells. The response profiles of differentiated clonal cells to application of GABA, glycine, dopamine, glutamate, acetylcholine, and 50 mM K+ RR, as evidence by increased intracellular calcium concentrations, were examined. $Ca^{2+}$ measurements were taken from as many as 113 cells from 4 different clones. All clones examined (4/4) displayed heterogeneity in their response profiles, which varied somewhat between individual clones.

Figure 7:
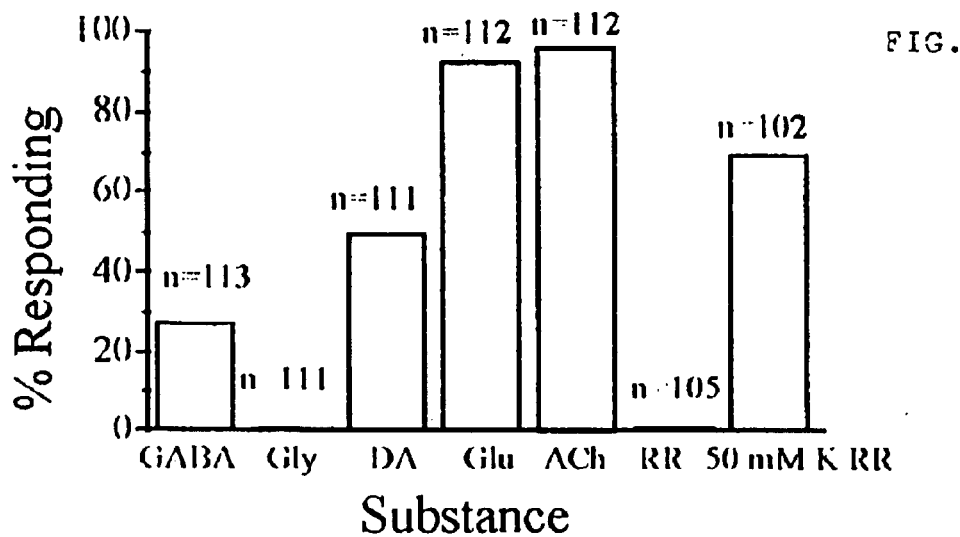
FIG. 7 shows a bar graph of the percentage of cells from four E-NCAM$^+$ clones that responded to neurotransmitters as measured by fura-2 calcium ion imaging: GABA ($\gamma$-amino butyric acid), Gly (glycine), DA (dopamine), Glu (glutamate), Ach (acetyl choline), RR (rat ringers solution), 50 mM K RR (rat ringers solution modified by replacing Na$^+$ with K$^+$).

FIG. 7 shows a bar graph of the percentage of cells from all 4 clones that responded to each of the applied neurotransmitters.

Figure 8:
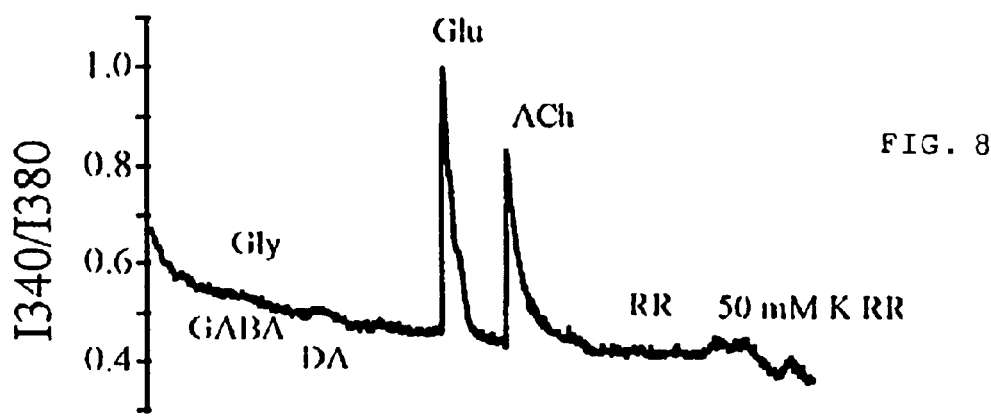
FIGS. 8 and 9 show illustrative traces of the ratio ($I_{340}/I_{380}$) of Ca$^{2+}$ responses from two cells recorded from one E-NCAM$^+$ clone.
Figure 9:
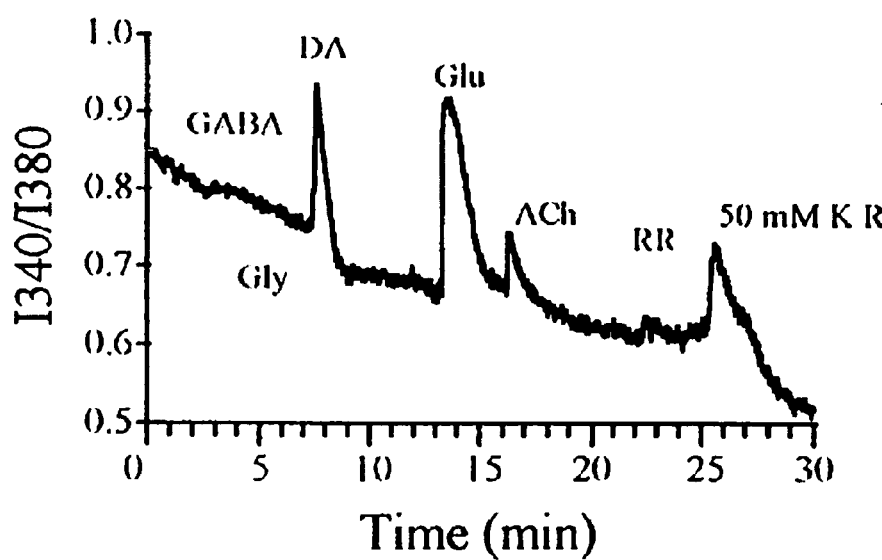

As with the mass cultures of differentiated E-NCAM+ cells, high percentages of clonal cells responded to glutamate (93%), acetylcholine (96%), 50 mM K+ RR (70%), and dopamine (50%), whereas few cells responded to GABA (27%) and glycine (1%). FIGS. 8 and 9 show representative traces of the ratio ($I_{340}/I_{380}$) of $Ca^{2+}$ responses from two cells recorded from one clone. This heterogeneous expression of receptors also suggested a multipotential characteristic of individual NRP cells. Thus, the maturation of clonal populations of cells closely resembled the maturation of cells in mass culture.

By multiple independent methods, this clonal analysis demonstrates the multipotential characteristic of individual NRP cells. This analysis confirms the mass culture results that clearly define the developmental potential of the NRP cell. Although committed to generating neurons, the particular phenotypes of its progeny are dictated at some later stage in their development. Thus, the existence has been established of a neuronal precursor cell that can be purified and subsequently manipulated to define the transition between lineage restricted neuronal precursor and differentiated neuronal progeny.

EXAMPLE 16

Extracellular Signals Influence the Fate of NRP Cells

The results disclosed herein show that neuronal precursors can develop in vitro into mature neurons of multiple phenotypes in both mass and clonal cultures and that either application of RA or removal of FGF can promote differentiation into multiple phenotypes. In normal development, however, differentiation is spatially and temporally regulated, with motoneurons being generated ventrally and sensory neurons being generated dorsally, suggesting that specific environmental signals may bias differentiation of neuronal precursors. In this example, the effects of two potentially regulatory molecules that are expressed in the spinal cord at the time of neurogenesis and have been shown to bias cells to either dorsal (BMP-2/4; J. M. Graff, Embryonic Patterning: To BMP or Not to BMP, That is the Question, 89 Cell 171–174 (1997)) or ventral (Shh; M. J. Fietz et al., The Hedgehog Gene Family in Drosophila and Vertebrate Development, Development (Suppl.) 43–51 (1994)) phenotypes.

Figure 10:
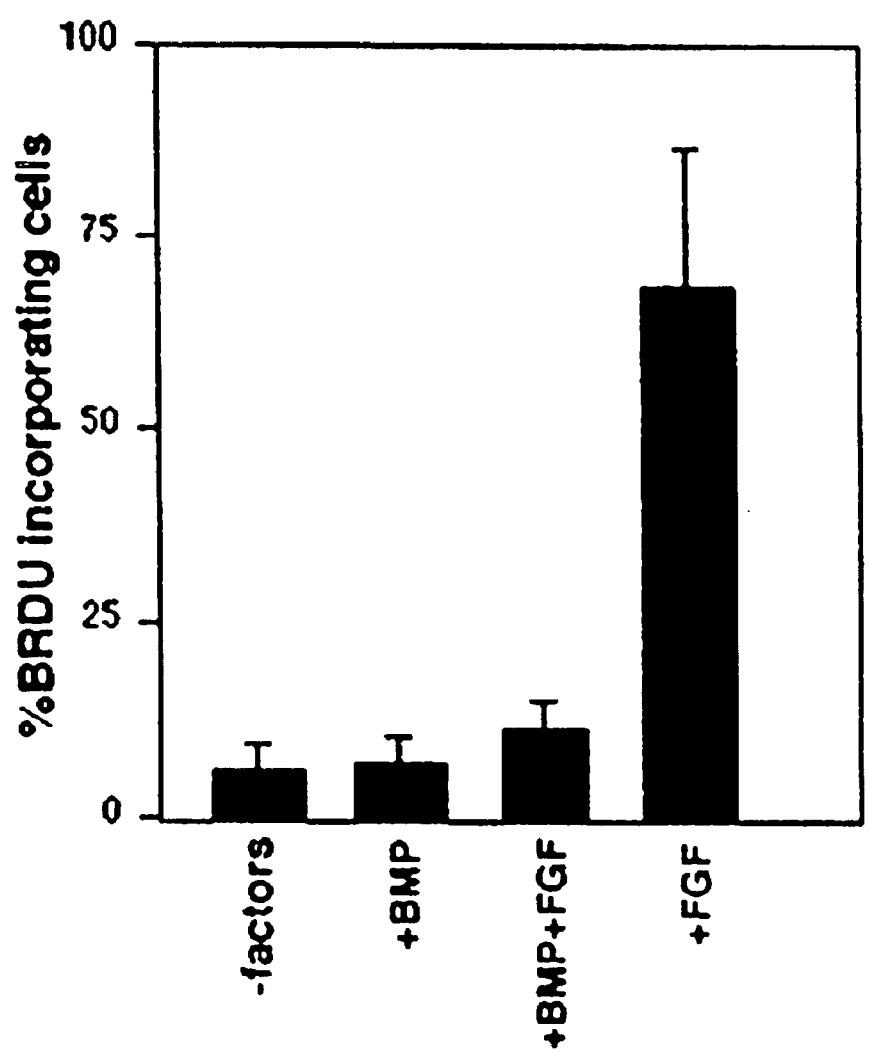
FIG. 10 shows the effect of bone morphogenetic protein 2 (BMP-2) on cell division of E-NCAM$^+$ cells as measured by BRDU incorporation.

When BMP-2 was added to cultures of E-NCAM+ cells, a dramatic reduction in cell division was seen. The effect of BMP-2 overrode the effect of the mitogen, FGF, and even in the presence of FGF, caused a 60% reduction in cell division (FIG. 10). Identical effects were seen with BMP-4. BMP-2 was not a survival factor, since cells grown in BMP-2 alone did not survive. The decrease in mitosis was accompanied by the appearance of differentiated cells. Cell size increased and cells put out extensive processes. Cells grown in BMP-2 for 48 hours were also examined for neurotransmitter expression. Glutamatergic, GABAergic, dopaminergic, and cholinergic neurons were detected. The number of cholinergic neurons was significantly larger than in untreated controls (5–10% v. 0–1%), however, there appeared to be no bias towards ventral phenotypes since the promotion of all other phenotypes was also significantly larger. Thus, BMP-2 acted as an antimitotic agent and promoted differentiation of E-NCAM+ NRP cells, but did not appear to inhibit ventral fates.

Figure 11:
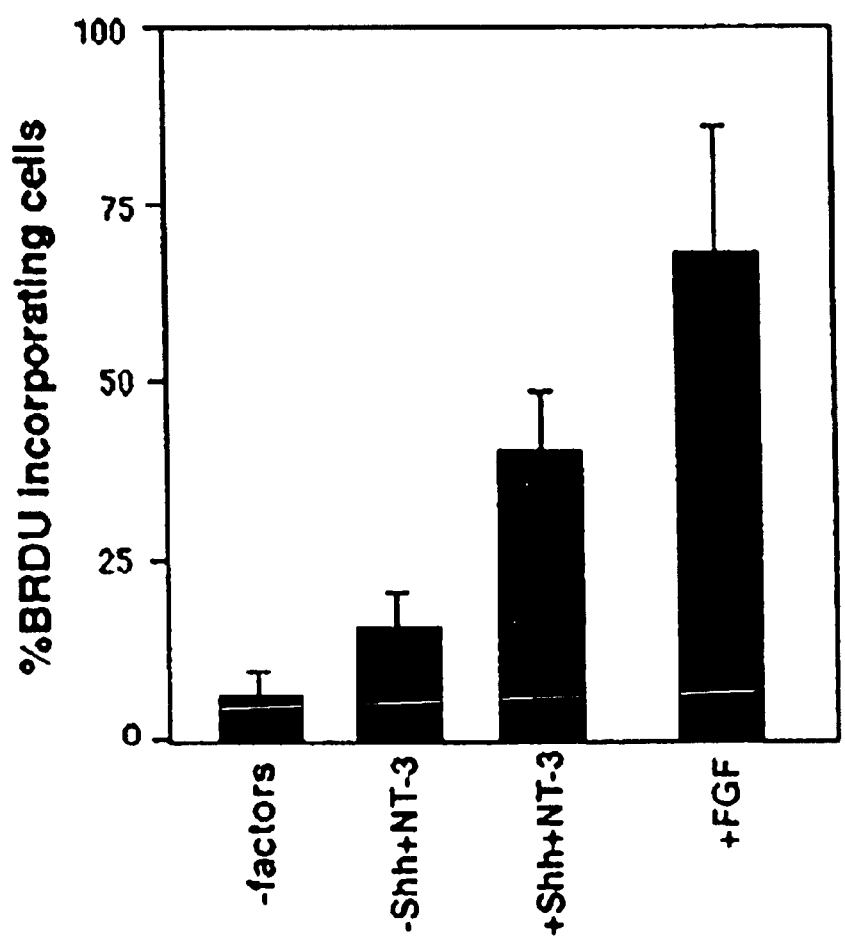
FIG. 11 shows the effect of sonic hedgehog (Shh) on cell division of E-NCAM$^+$ cells as measured by BRDU incorporation.

In contrast to the antimitotic and differentiation promoting effect of BMP, Shh appeared to be a mitogen. The mitotic effect of Shh at 100 ng/ml (the maximal response) was three-fold higher than controls, but was less than the effect of FGF at 10 ng/ml (FIG. 11). Experiments with Shh were done in the presence of NT-3, which acts as a survival agent, Y. A. Barde, Neurotrophins: A Family of Proteins Supporting the Survival of Neurons, 390 Prog. Clin. Biol. Res. 45–56 (1994), and not a mitogen, because Shh itself did not appear to be a survival factor for E-NCAM$^+$ cells, i.e. E-NCAM$^+$ cells grown in Shh alone did not survive. The effect of Shh on mitosis was only apparent after two days of exposure and was maintained over 5 days of the assay. No difference in cell division was seen during the first 24 hours.

Shh did not appear to promote motoneuron differentiation over the 5 days of the assay. Cells continued to proliferate and no p75 or ChAT immunoreactive neurons could be detected. The failure to see cholinergic neurons was not due to an inability of the E-NCAM$^+$ cells to differentiate into p75 or ChAT positive cells, as sister cultures readily differentiated into ChAT and p75 immunoreactive cells when treated with a differentiation agent such as BMP-2 or RA. Thus, E-NCAM$^+$ cells respond to Shh by proliferating. Shh unexpectedly did not promote motoneuron differentiation, at least over the time period tested.

These results indicate that extracellular signaling molecules Shh and BMP modulate the phenotypic differentiation of E-NCAM$^+$ cells. BMP-2 inhibits cell proliferation and promotes differentiation and does not inhibit the differentiation of ventral phenotypes. In contrast, Shh promotes proliferation and inhibits the differentiation of any neuronal phenotypes, including p75 and ChAT immunoreactive neurons.

EXAMPLE 17

Mouse Neural Tubes Contain E-NCAM Immunoreactive Neural Precursors

To determine whether NRPs are present in mouse neural tubes, E11 mouse spinal cords were dissociated and examined for properties of E-NCAM immunoreactive cells, according to the procedures of Example 2.

A large number of E-NCAM immunoreactive cells were found at E11, and these cells comprised about 60% of the total population of cells. E-NCAM-positive cells appeared morphologically similar to neurons with extensive processes. At this stage of development, no co-expression of E-NCAM with either Gal-C or GFAP was observed in double-labeling experiments, suggesting that E-NCAM immunoreactivity may identify neuronal precursors.

Figure 12:
FIG. 12 shows results of RT-PCR amplification of total RNA isolated from mouse E-NCAM$^+$ cells for determining expression of (from left to right after the molecular weight markers at the far left) p75, Isl-1, ChAT, calbindin, GAD, and glutaminase.

To determine if mouse E-NCAM-positive cells, like their rat counterparts, underwent cell division, cells were pulse labeled with BRDU and then double-labeled to detect cells that co-expressed BRDU and E-NCAM immunoreactivity. Results showed that E-NCAM-positive cells divided for at least three days in culture. E-NCAM-positive cells, thus, appeared similar to the NRPs previously described in rats. To confirm that E-NCAM-positive cells could generate multiple neuronal phenotypes, immunoselected E-NCAM cells prepared according to the procedure of Example 3 were allowed to differentiate in culture for 10 days. Plates were then harvested, and cDNA was prepared according to the procedure of Example 13 to assess neurotransmitter synthesis. As can be seen in FIG. 12, expression of p75, islet-1, ChAT, calbindin, GAD, and glutaminase were readily detected in differentiated populations. Thus, mouse E-NCAM immunoreactive cells can generate neurons that express cholinergic, excitatory, and inhibitory phenotypes.

EXAMPLE 18

E-NCAM Immunoreactive Neuroblasts can be Generated from ES Cells

Figure 13:
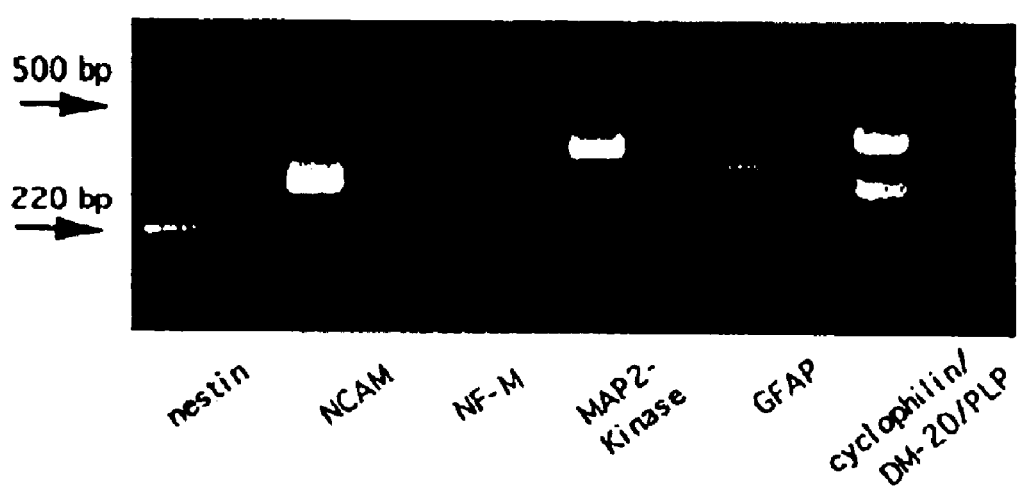
FIG. 13 shows results of RT-PCR amplification of total RNA isolated from differentiated mouse ES cells for determining expression of (from left to right) nestin, -CAM, neurofilament-M (NF-M), microtubule associated protein 2 (Map-2), GFAP, DM-20/PLP.

In Example 17 it was shown that mouse spinal cords contain E-NCAM immunoreactive NRPs that are similar to rat NRP cells. To determine if similar lineage restricted precursors could be generated from ES cells, mouse ES cells were obtained from the Developmental Studies Hybridoma Bank (DSHB; University of Iowa, Iowa City, Iowa) and were then grown in culture and examined for the expression of E-NCAM, A2B5, and other neuroglial markers. As has been previously described, undifferentiated ES cells did not express detectable immunoreactivity for any of the markers tested. In contrast, when ES cells were plated in neural differentiation conditions ES cells altered their morphology and began to express multiple neuronal and glial markers (FIG. 13). Differentiated ES cells were harvested and total RNA prepared for RT-PCR according to the procedure of Example 13. Of particular importance is the early expression of E-NCAM (early neuronal marker) and PLP/DM20 genes (known to be expressed by embryonic glial precursors). Consistent with the detection of early neuronal and glial markers by PCR, high polysialiated NCAM expressing cells represented a small percentage of the total cells. Less than 5% of cells in culture expressed E-NCAM immunoreactivity after 5 days in culture. The percentage of A2B5 immunoreactive cells was significantly higher; about 10% of differentiated cells expressed this marker.

To determine if E-NCAM immunoreactive cells represented neuronal precursors, the co-expression of neuronal and glial markers was examined. E-NCAM immunoreactive cells co expressed MAP-2 and β-III tubulin immunoreactivity, but did not co-express GFAP and nestin immunoreactivity. E-NCAM-positive cells did not express Gal-C or other oligodendrocytic markers. Thus, E-NCAM immunoreactive cells that were derived from mouse ES cells appeared similar to spinal-cord-derived E-NCAM-positive NRPs.

Figure 14:
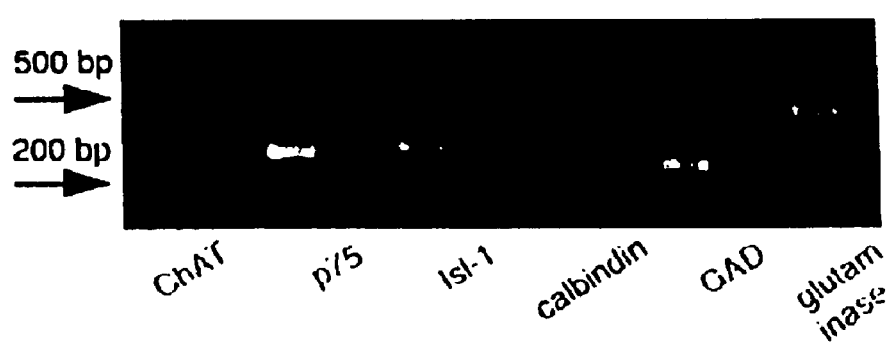
FIG. 14 shows results of RT-PCR amplification of total RNA isolated from differentiated mouse ES cells for determining expression of (from left to right) ChAT, p75, islet-1, calbindin, GAD, and glutaminase.

To confirm that ES-cell-derived neuronal precursors could generate multiple kinds of neurons, E-NCAM immunoreactive cells were immunoselected according to the procedure of Example 3 and such purified cells were allowed to differentiate for 10 days. Cells were then harvested and analyzed by immunocytochemistry and RT-PCR for the expression of phenotypic markers. FIG. 14 shows the results of an illustrative PCR experiment wherein ChAT, p75, islet-1, calbindin, GAD, and glutaminase expression was readily detected in differentiated populations. Thus, ES-cell-derived E-NCAM immunoreactive cells differentiated into postmitotic neurons that expressed multiple neurotransmitters, including cholinergic, excitatory, and inhibitory phenotypes. Therefore, ES cells can be used as a source of lineage restricted NRPs.

EXAMPLE 19

NRPs in Human Neural Tubes

To determine if NRPs are present in human neural tubes, human embryonic spinal cords were dissociated and the phenotypes of cells when grown in DMEM/F12 in a high concentration of FGF were examined according to the procedure of Example 2.

Human spinal cord cells (HSCs) initially appeared morphologically similar to rat and mouse spinal cords, but rapidly differentiated into fibroblastic appearing cells with a significant proportion of cells having a neuronal morphology. HSCs continued to divide rapidly and most cells (95%) were nestin immunoreactive. At this stage, cultures did not contain astrocytes, oligodendrocytes, or their precursors as detected by the expression of GFAP or O4/Gal-C immunoreactive cells. A substantial number of E-NCAM immunoreactive cells were present, however, and constituted about 40% of the total population. E-NCAM immunoreactive cells appeared morphologically similar to neurons, although some flat E-NCAM immunoreactive cells were also present. Both populations of E-NCAM-positive cells were MAP2K immunoreactive and also expressed a variety of other early neuronal markers, as summarized in Table 10.

TABLE 10

| Antigen | % E-NCAM$^+$ Cells |
|---|---|
| Nestin | 100 |
| MAP2 | 100 |
| Neurofilament H | 80 |
| Neurofilament-M | Occasional Cell |
| β-III tubulin | 100 |
| Gal-C/O4 | 0 |
| GFAP | 0 |

At this stage of development, no co-expression of E-NCAM with either Gal-C or GFAP was observed in double-labeling experiments, suggesting that E-NCAM immunoreactivity identifies neuronal precursors. That is, E-NCAM immunoreactive human spinal cord cells expressed neuronal but not non-neuronal antigens. To determine if human E-NCAM$^+$ cells, like their rat counterparts, underwent cell division, mixed cultures of HSCs were pulse labeled with BRDU and then double labeled to detect cells that co-expressed BRDU and E-NCAM immunoreactivity. The results of this experiment showed that E-NCAM-positive cells divided for at least three days in culture. Consistent with the results of Table 10 that E-NCAM immunoreactive cells also express NF-H, BRDU-incorporating cells also co-expressed neurofilament-H. Thus, as in fetal rodent spinal cord cultures, dividing nestin immunoreactive precursor cells from humans are present and E-NCAM immunoreactive cells represent a significant fraction of total precursor population at this age. E-NCAM$^+$ cells appear similar to the NRPs previously described for rats and mice.

Transplanted-cells can be administered to any animal, including humans, with abnormal neurological or neurodegenerative symptoms obtained in any manner, including as a result of chemical electrolytic lesions, experimental destruction of neural areas, or aging processes. Transplantation can be bilateral, or, for example in patients suffering from Parkinson's Disease, can be contralateral to the most-affected side. Surgery is preferably performed such that particular brain regions are located, such as in relation to skull sutures, and surgery performed with stereotactic techniques. Alternatively, cells can be implanted in the absence of stereotactic surgery. Cells can be delivered to any affected neural areas using any method of cell injection or transplantation known in the art.

In another embodiment of the invention, NRP cells are transplanted into a host, and induced to proliferate and/or differentiate in that host by (1) proliferation and/or differentiation in vitro prior to being administered, or (2) differentiation in vitro prior to being administered and proliferation and differentiation in vivo after being administered, or (3) proliferation in vitro prior to being administered and then differentiation in vivo without further proliferation after being administered, or (4) proliferation and differentiation in vivo after being injected directly after being freshly isolated.

NRP cells can also be used for delivery of therapeutic or other compounds. Methods for bypassing the blood-brain barrier for purposes of delivery of therapeutic compounds include implanting cells in an encapsulation device according to methods known in the art or directly implanting genetically engineered cells such that the cells themselves produce the therapeutic compound. Such compounds may be small molecules, peptides, proteins, or viral particles. Cells can be genetically transduced by any means known in the art, including calcium phosphate transfection, DEAE-dextran transfection, polybrene transfection, electroporation, lipofection, infection of viruses, and the like. Cells are first genetically manipulated to express a therapeutic substance and then transplanted either as free cells able to diffuse and incorporate within the CNS parenchyma or are contained within an encapsulation device. R. P. Lanza & W. L. Chick, Encapsulated Cell Therapy, Sci. Amer.: Sci. & Med., Jul./Aug., 16–25 (1995); P. M. Galletti, Bioartificial Organs, 16 Artificial Organs 55–60 (1992); A. S. Hoffman, Molecular Engineering of Biomaterials in the 1990s and Beyond: A Growing Liaison of Polymers with Molecular Biology, 16 Artificial Organs 43–49 (1992); B. D. Ratner, New Ideas in Biomaterials Science—A Path to Engineered Biomaterials, 27 J. Biomed. Mat. Res. 837–850 (1993); M. J. Lysaght et al., Recent Progress in Immunoisolated Cell Therapy, 56 J. Cell Biochem. 196–203 (1994), hereby incorporated by reference.

Transplanted cells can be identified by prior incorporation of tracer dyes such as rhodamine or fluorescein-labeled microspheres, fast blue, bis-benzamide, or genetic markers incorporated by any genetic transduction procedure known in the art to allow expression of such enzymatic markers as β-galactosidase or alkaline phosphatase.

Any expression system known in the art can be used to express the therapeutic compound, so long as it has a promoter that is active in the cell, and appropriate internal signals for initiation, termination, and polyadenylation. Examples of suitable expression vectors include recombinant vaccinia virus vectors including pSC11, or vectors derived from viruses such as simian virus 40 (SV40), Rous Sarcoma Virus (RSV), mouse mammary tumor virus (MMTV), go adenovirus, herpes simplex virus (HSV), bovine papilloma virus, Epstein-Barr virus, lentiviruses, or any other eukaryotic expression vector known in the art. Many of such expression vectors are commercially available.

Cells can also be transduced to express any gene coding for a neurotransmitter, neuropeptide, neurotransmitter-synthesizing enzyme or neuropeptide synthesizing enzyme for which expression in the host is desired.

NRP cells and/or their derivatives cultured in vitro can be used for the screening of potentially neurologically therapeutic compositions. These compositions can be applied to cells in culture at varying dosages, and the response of the cells monitored for various time periods. The induction of expression of new or increased levels of proteins such as enzymes, receptors, and other cell surface molecules, or of neurotransmitters, amino acids, neuropeptides, and biogenic amines can be analyzed with any technique known in the art that can identify the alteration of the level of such molecules, including protein assays, enzymatic assays, receptor binding assays, enzyme-linked immunosorbent assays, electrophoretic analysis, analysis with high performance liquid chromatography, Western blots, and radioimmune assays. Nucleic acid analysis, such as Northern blots, can be used to examine the levels of mRNA coding for these molecules, or for the enzymes that synthesize these molecules. Alternatively, cells treated with these pharmaceutical compositions can be transplanted into an animal and their survival, ability to form neurons, and to express any of the functions of these cell types can be analyzed by any procedure available in the art.

NRP cells can be cryopreserved by any method known in the art.

EXAMPLE 20

Use of NRP Cells and/or Their Derivatives for Treatment of Abnormal Neurological or Neurodegenerative Symptoms NRP cells are isolated by the methods of Examples 2, 3, 8, 18, or 19. Cells are obtained from human embryonic or adult CNS or from xenographic sources from which immunorejection of cells is not a clinical problem, such as pigs genetically engineered so as not to present a foreign stimulus to the human immune system. Cells collected from embryos are obtained by dissection of CNS tissue following routine abortion procedures and tissue collection in a sterile collection apparatus. Cells from the postnatal CNS are obtained by digestion of tissue following routine autopsy. Tissue is prepared, cells are immunopurified, and the resulting purified cells are cultured as in Example 2.

Cells can be transplanted directly or can first be expanded in vitro prior to transplantation. Populations expanded in vitro can further be expanded in conditions that enhance the generation of neurons or cells committed to the generation of neurons.

Transplantation is routinely carried out at cell suspensions of 5–50,000 cells/$\mu$l in physiological salt solutions, such as PBS. Cells can be transplanted into or near any CNS regions affected by the disease or condition. Transplantation procedures, with appropriate modifications for use in human patients, are in their essence similar to procedures well known to those skilled in the art of transplantation of O-2A progenitor cells, e.g., A. K. Groves et al., Repair of Demyelinated Lesions by Transplantation of Purified O-2A Progenitor Cells, 362 Nature 453–455 (1993), hereby incorporated by reference.

More specifically, transplantation is performed using a computed tomographic stereotaxic guide. The patient is operated on using any of the procedures known in the art. In cases where precisely localized transplantation is desirable, the patient undergoes CT scanning to establish the coordinates of the region to receive the transplant. The injection cannula can be in any configuration used by those skilled in the relevant arts. The cannula is then inserted into the brain to the correct coordinates, then removed and replaced with a 19-gauge infusion cannula that has been preloaded with cell suspension in a small selected volume. The cells are then slowly infused, at rates generally of 1–10 ml per minute as the cannula is withdrawn. For some diseases in which it is desirable to spread cells over the largest possible area, multiple stereotactic needle passes may be made throughout the area. Patients are examined post-operatively for hemorrhage or edema. Neurological evaluations are performed at various post-operative intervals, as well as PET scans if these can be used to determine the metabolic activity of the implanted cells. These and similar procedures can be used for any implantation of NRP cells for any of the purposes indicated in this invention.

Success of the procedure is determined by non-invasive analysis with, for example, nuclear magnetic resonance image scanners, and/or by analysis of functional recovery according to methods well known in the art.

EXAMPLE 21

Use of Genetically Engineered NRP Cells and/or Their Derivatives for Transplantation In this example, NRP cells are genetically modified ex vivo before introduction into or near regions of disease to express gene products that will make the transplanted cells resistant to destruction in vivo and/or to express gene products that provide trophic support to the host cells and/or to express gene products that limit destructive processes occurring in the host. Genetic modification is carried out by any of the techniques known to those skilled in the art, including but not limited to calcium phosphate transfection, DEAE-dextran transfection, polybrene transfection, electroporation, lipofection, infection of viruses, and the like. Gene products that would make cells resistant to destruction in vivo and/or to express gene products that provide trophic support to host cells and/or to express gene products that limit destructive processes occurring in the host include but are not limited to insulin-like growth factor-I, decay accelerating factor, catalase, superoxide dismutase, members of the neurotrophin family, glial-derived neurotrophic factor, ciliary neurotrophic factor, leukemia inhibitory factor, fas ligand, cytokines that inhibit inflammatory processes, receptor fragments that inhibit inflammatory processes, antibodies that inhibit inflammatory processes, and so forth.

EXAMPLE 22

Use of NRP Cells and/or Their Derivatives for the Screening of Potentially Neurologically Therapeutic Compositions NRP cells or derivatives thereof or mixtures thereof cultured in vitro can be exposed to compositions of interest at varying dosages, and the response of the cells monitored for various time periods. The induction of expression of new or increased levels of proteins such as enzymes, receptors, and other cell surface molecules or of neurotransmitters, amino acids, neuropeptides, and biogenic amines can be analyzed with any technique known in the art that can identify the alteration of the level of such molecules, including protein assays, enzymatic assays, receptor binding assays, enzyme-linked immunosorbent assays, electrophoretic analysis, analysis with high performance liquid chromatography, Western blots, and radioimmune assays. Nucleic acid analysis, such as Northern hybridization can be used to examine the levels of mRNA coding for these molecules, or for the enzymes that synthesize these molecules. Cells can also be used to screen for compounds able to promote the division of NRP cells and/or their derivatives by determining the ability of compounds to cause increases in NRP cell number or to promote DNA synthesis, as measured by, e.g. incorporation of bromodeoxyuridine or tritiated thymidine. Cells can also be used to screen for compounds that promote survival of NRP cells and/or their derivatives by applying compounds to cells in conditions where they would be expected to die (e.g., exposure to neurotoxic agents, withdrawal of all trophic factors) and examining cell survival using any of the techniques well known to practitioners of the art. Cells can also be used to screen for compounds that specifically inhibit binding to particular receptors, by looking at the ability of said blocking compounds to block the response elicited by binding of agonist to said receptors. Cells can also be used to screen for compounds able to activate particular receptors using ligand binding assays well known to practitioners of the art, or by looking at such physiological alterations as are associated with activation of the receptor, such as fluxes in calcium levels, or other alterations well known to practitioners of the art. Alternatively, cells treated with these pharmaceutical compositions can be transplanted into an animal and their survival, ability to form neurons and to express any of the functions of these cells types can be analyzed by any procedures available in the art.

EXAMPLE 23

In this example, cells were harvested from E13.5 rat spinal cords, and E-NCAM immunoreactive neuronal restricted precursor cells were isolated by immunopanning according to the procedure of Example 3. These cells were then labeled with a cell tracker and were transplanted to different cortical regions using a glass microelectrode. Animals were sacrificed after 3.5, 10 or 21 days, and the brain was sectioned according to methods well known in the art. Such transplanted cells were shown to survive and differentiate at all three times.

EXAMPLE 24

In this example, cells were harvested, isolated, and plated in a 35 mm dish as described in Example 3. Cells were then incubated with a retroviral construct containing a green fluorescent protein (GFP) reporter gene under a cytomegalovirus (CMV) promoter. Cells were allowed to recover for 8 hours and then were analyzed for GFP expression. GFP expression was detected as early as 24 hours after infection, and GFP expression persisted for up to two weeks, at which time the experiment was concluded. These results show that ectopic genes can be expressed in NRPs under a heterologous promoter, and that infected cells continue to stably express the ectopic protein for several weeks.

We claim:

1. A method of isolating a pure population of rodent or human CNS neuron-restricted precursor cells comprising the steps of:
   (a) isolating a population of rodent or human multipotent CNS stem cells which generate both neurons and glia;
   (b) incubating the multipotent CNS stem cells in NEP medium;
   (c) replating the multipotent CNS stem cells on laminin in NEP medium in the absence of chick embryo extract to induce cell differentiation;
   (d) removing A2B5+ cells from the differentiating cells via specific antibody capture with an antibody that specifically recognizes A2B5;
   (e) purifying from the supernatant following step (d) a subpopulation of cells expressing embryonic neural cell adhesion molecules via a procedure selected from the group consisting of specific antibody capture, fluorescence activated cell sorting, and magnetic bead capture, wherein said procedure uses an embryonic neural cell adhesion molecule antibody that specifically recognizes polysialated neural call adhesion molecule (NCAM); and
   (f) incubating the purified subpopulation of cells in a FGF-containing medium to obtain an isolated, purified population of rodent or human CNS neuron-restricted precursor cells.

2. The method of claim 1 wherein the subpopulation of cells expressing embryonic neural cell adhesion molecules is purified by specific antibody capture.

3. The method of claim 1 wherein the rodent or human multipotent CNS stem cells are neuroepithelial cells.

4. A pure population of rodent or human CNS neuron-restricted precursor cells isolated by the method of claim 1.

5. A method of isolating a pure population of rodent or human CNS neuron-restricted precursor cells comprising the steps of:
   (a) removing a sample of spinal cord tissue from a rodent or human embryo at a stage of embryonic development after closure of the neural tube;
   (b) dissociating cells comprising the sample of spinal cord tissue removed from the embryo;
   (c) removing A2B5+ cells from the dissociated cells via specific antibody capture with an antibody that specifically recognizes A2B5;
   (d) purifying from the supernatant following step (c) a subpopulation expressing embryonic neural cell adhesion molecule via a procedure selected from the group consisting of specific antibody capture, fluorescence activated cell sorting, and magnetic bead capture, using an embryonic neural cell adhesion molecule antibody that specifically recognizes polysialated neural cell adhesion molecule;
   (e) plating the purified subpopulation of cells in feeder-cell-independent culture on a substratum and in a FGF-containing medium; and
   (f) incubating the plated cells in the FGP-containing medium to obtain an isolated, pure population of neuron-restricted precursor cells.

6. The method of claim 5 wherein the subpopulation of cells expressing embryonic neural cell adhesion molecules is purified by is specific antibody capture.

7. A pure population of rodent or human CNS neuron-restricted precursor cells isolated by the method of claim 5.

* * * * *

SEQUENCE LISTING

<160> NUMBER OF SEQ ID NOS: 14

<210> SEQ ID NO 1
<211> LENGTH: 21
<212> TYPE: DNA
<213> ORGANISM: Rattus norvegicus

<400> SEQUENCE: 1
gcacatactc agacgaagcc a                                            21

<210> SEQ ID NO 2
<211> LENGTH: 24
<212> TYPE: DNA
<213> ORGANISM: Rattus norvegicus

<400> SEQUENCE: 2
agcagccaag atggagcaat agac                                         24

<210> SEQ ID NO 3
<211> LENGTH: 23
<212> TYPE: DNA
<213> ORGANISM: Rattus norvegicus

<400> SEQUENCE: 3
ctgaatactg gctgaatgac atg                                          23

<210> SEQ ID NO 4
<211> LENGTH: 23
<212> TYPE: DNA
<213> ORGANISM: Rattus norvegicus

<400> SEQUENCE: 4
aaattaatga caacatccaa gac                                          23

<210> SEQ ID NO 5
<211> LENGTH: 20
<212> TYPE: DNA
<213> ORGANISM: Rattus norvegicus -continued

<400> SEQUENCE: 5
gcagcatagg cttcagcaag　　　　　　　　　　　　　　　　　　　20

<210> SEQ ID NO 6
<211> LENGTH: 19
<212> TYPE: DNA
<213> ORGANISM: Rattus norvegicus

<400> SEQUENCE: 6
gtagcaggtc cgcaaggtg　　　　　　　　　　　　　　　　　　　　19

<210> SEQ ID NO 7
<211> LENGTH: 21
<212> TYPE: DNA
<213> ORGANISM: Rattus norvegicus

<400> SEQUENCE: 7
gaatcttttc tcctggtggt g　　　　　　　　　　　　　　　　　　 21

<210> SEQ ID NO 8
<211> LENGTH: 21
<212> TYPE: DNA
<213> ORGANISM: Rattus norvegicus

<400> SEQUENCE: 8
gatcaaaagc cccgtacaca g　　　　　　　　　　　　　　　　　　 21

<210> SEQ ID NO 9
<211> LENGTH: 18
<212> TYPE: DNA
<213> ORGANISM: Rattus norvegicus

<400> SEQUENCE: 9
gcagaatccc acctgcag　　　　　　　　　　　　　　　　　　　　 18

<210> SEQ ID NO 10
<211> LENGTH: 19
<212> TYPE: DNA
<213> ORGANISM: Rattus norvegicus

<400> SEQUENCE: 10
gttgctggca tcgaaagag　　　　　　　　　　　　　　　　　　　　19

<210> SEQ ID NO 11
<211> LENGTH: 24
<212> TYPE: DNA
<213> ORGANISM: Rattus norvegicus

<400> SEQUENCE: 11
gcacagacat ggttgggata ctag　　　　　　　　　　　　　　　　　24

<210> SEQ ID NO 12
<211> LENGTH: 20
<212> TYPE: DNA
<213> ORGANISM: Rattus norvegicus

<400> SEQUENCE: 12
gcagggctgt tctggagtcg　　　　　　　　　　　　　　　　　　　 20

<210> SEQ ID NO 13
<211> LENGTH: 20
<212> TYPE: DNA
<213> ORGANISM: Rattus norvegicus

```
<400> SEQUENCE: 13
ccaccgtgtt cttcgacatc                                            20

<210> SEQ ID NO 14
<211> LENGTH: 19
<212> TYPE: DNA
<213> ORGANISM: Rattus norvegicus

<400> SEQUENCE: 14
ggtccagcat ttgccatgg                                             19
```